(12) United States Patent
Goto et al.

(10) Patent No.: US 10,350,394 B2
(45) Date of Patent: Jul. 16, 2019

(54) BALLOON COATING METHOD, BALLOON ROTATING METHOD, AND BALLOON COATING DEVICE

(71) Applicant: TERUMO KABUSHIKI KAISHA, Shibuya-ku, Tokyo (JP)

(72) Inventors: Hiroshi Goto, Kanagawa (JP); Yasuo Kurosaki, Kanagawa (JP); Eisuke Furuichi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/789,592

(22) Filed: Oct. 20, 2017

(65) Prior Publication Data

US 2018/0071499 A1 Mar. 15, 2018

Related U.S. Application Data

(63) Continuation of application No. PCT/JP2016/062764, filed on Apr. 22, 2016.

(30) Foreign Application Priority Data

Apr. 23, 2015 (JP) ................................ 2015-088381

(51) Int. Cl.
*A61M 25/10* (2013.01)
*B05B 13/02* (2006.01)
(Continued)

(52) U.S. Cl.
CPC ........ *A61M 25/1029* (2013.01); *A61M 25/10* (2013.01); *B05B 13/0228* (2013.01);
(Continued)

(58) Field of Classification Search
CPC ................... A61M 2025/1031; B05B 13/0228
See application file for complete search history.

(56) References Cited

U.S. PATENT DOCUMENTS 8,382,927 B1 2/2013 Tayebi
8,597,720 B2 12/2013 Hoffmann et al.
(Continued)

FOREIGN PATENT DOCUMENTS

JP 2015-119805 A 7/2015
WO WO 2013/181498 A1 12/2013
(Continued)

OTHER PUBLICATIONS

International Search Report (PCT/ISA/210) dated Jun. 14, 2016, by the Japanese Patent Office as the International Searching Authority for International Application No. PCT/JP2016/062764.
(Continued)

*Primary Examiner* — Cachet I Sellman
(74) *Attorney, Agent, or Firm* — Buchanan Ingersoll & Rooney PC

(57) ABSTRACT

A balloon coating method for forming a coating layer containing a water-insoluble drug on the outer surface of a balloon of a balloon catheter. The method includes applying a first rotation force to the balloon catheter proximal to the balloon of the balloon catheter and applying a second rotation force to the balloon catheter distal to the balloon of the balloon catheter. The first rotation speed is the same as the second rotation speed. The method includes applying a coating solution containing the drug to the outer surface of the balloon from a dispensing tube while gradually moving the dispensing tube in the axial direction and simultaneously applying the first and second rotation forces to rotate the balloon catheter around the longitudinal axis of the balloon catheter.

16 Claims, 15 Drawing Sheets

(51) Int. Cl.
*B05D 1/40* (2006.01)
*B05C 5/02* (2006.01)
(52) U.S. Cl.
CPC .............. *B05C 5/0216* (2013.01); *B05D 1/40* (2013.01); *A61M 2025/105* (2013.01); *A61M 2025/1031* (2013.01)

(56) References Cited

U.S. PATENT DOCUMENTS

| | | | |
|---|---|---|---|
| 2009/0093870 A1* | 4/2009 | Menendez | B05B 13/0228 623/1.11 |
| 2009/0317537 A1 | 12/2009 | Andreacchi | |
| 2010/0034960 A1* | 2/2010 | Kindaichi | A61F 2/91 427/2.25 |
| 2010/0040766 A1 | 2/2010 | Chappa et al. | |
| 2010/0055294 A1* | 3/2010 | Wang | B05D 1/002 427/2.25 |
| 2011/0034992 A1* | 2/2011 | Papp | B05D 1/002 623/1.16 |
| 2011/0295200 A1* | 12/2011 | Speck | A61L 29/06 604/103.02 |
| 2012/0128863 A1* | 5/2012 | Nguyen | A61M 25/1029 427/2.3 |
| 2013/0337147 A1* | 12/2013 | Chappa et al. | |
| 2014/0121597 A1* | 5/2014 | Chappa | B05D 1/002 604/103.08 |
| 2014/0358122 A1 | 12/2014 | Yamashita et al. | |
| 2016/0296735 A1 | 10/2016 | Goto et al. | |

FOREIGN PATENT DOCUMENTS

| | | |
|---|---|---|
| WO | WO 2014/066760 A1 | 5/2014 |
| WO | WO 2014/163091 A1 | 10/2014 |
| WO | WO 2015/093584 A1 | 6/2015 |

OTHER PUBLICATIONS

Written Opinion (PCT/ISA/237) dated Jun. 14, 2016, by the Japanese Patent Office as the International Searching Authority for International Application No. PCT/JP2016/062764.

English translation of the Written Opinion (PCT/ISA/237) dated Jun. 14, 2016, by the Japanese Patent Office as the International Searching Authority for International Application No. PCT/JP2016/062764 (6 pages).

The extended European Search Report dated Aug. 31, 2018, by the European Patent Office in corresponding European Patent Application No. 16783273.2-1132. (12 pages).

* cited by examiner

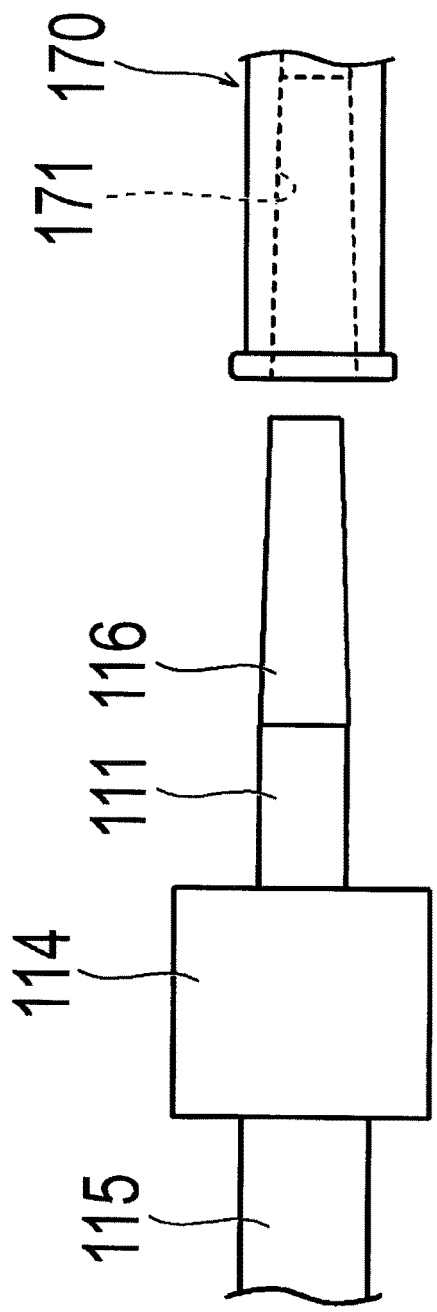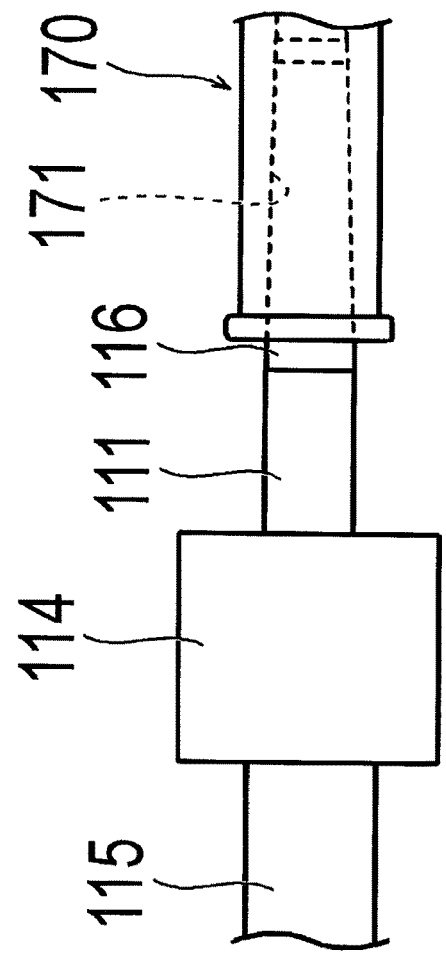
FIG. 4(A)
FIG. 4(B)

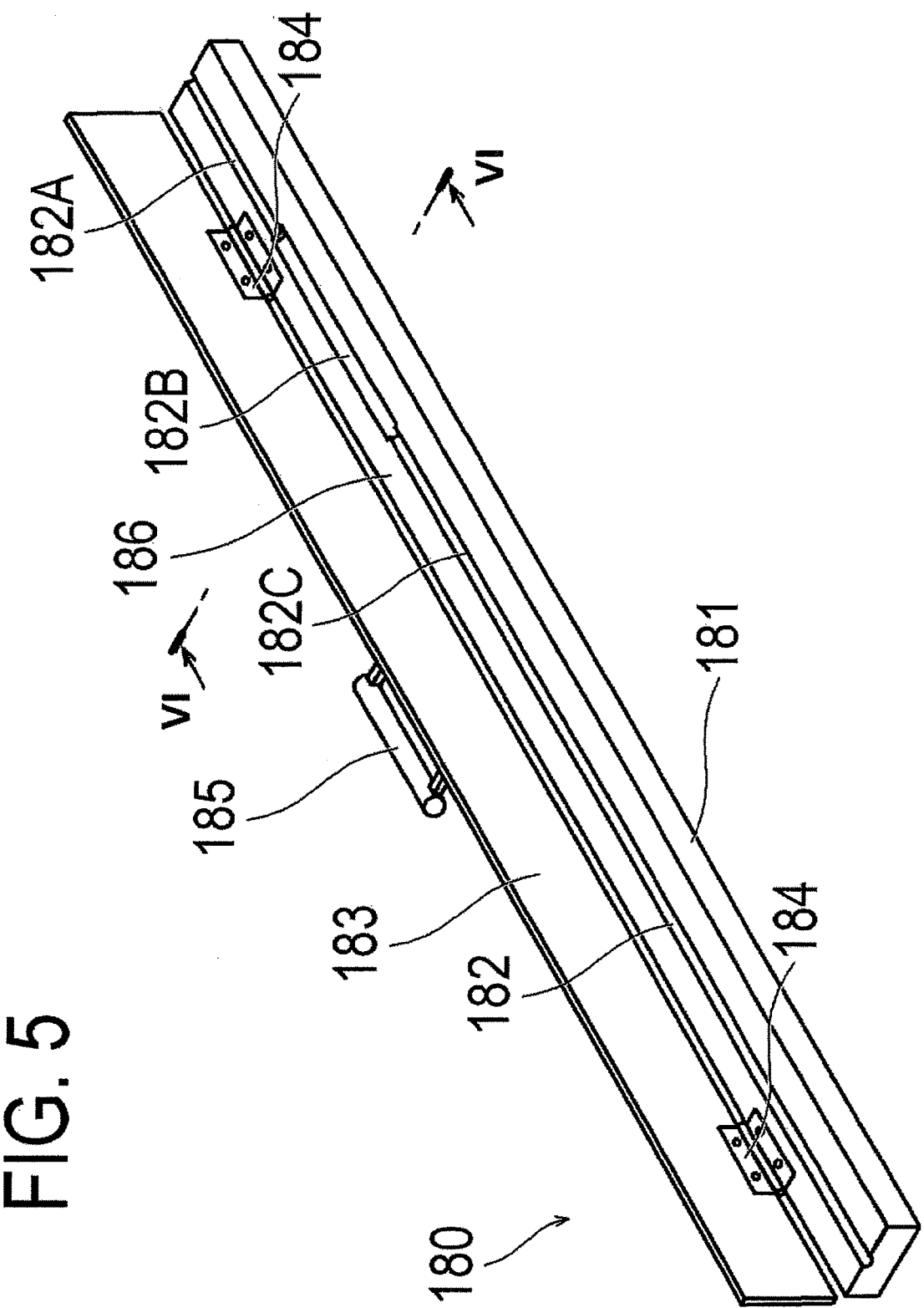

BALLOON COATING METHOD, BALLOON ROTATING METHOD, AND BALLOON COATING DEVICE

CROSS-REFERENCES TO RELATED APPLICATIONS

This application is a continuation of International Application No. PCT/JP2016/062764 filed on Apr. 22, 2016, and claims priority to Japanese Application No. 2015-088381 filed on Apr. 23, 2015, the entire content of both which is incorporated herein by reference.

TECHNICAL FIELD

The present invention generally relates to a balloon coating method for forming a coating layer containing a drug on a surface of a balloon, a balloon rotating method, and a balloon coating device.

BACKGROUND ART

In recent years, a balloon catheter has been used to improve a lesion area (stenosed site) inside a body lumen of a living body. The balloon catheter normally includes an elongated shaft portion and a balloon. The balloon is normally disposed on a distal side of the shaft portion and is inflatable in a radial direction (i.e., expandable radially outward). The balloon is brought into a deflated state and is moved to reach a target place inside a living body by way of a thin body lumen. Thereafter, the balloon is inflated, thereby enabling the lesion area to be widened.

If the lesion area is forcibly widened, however, smooth muscle cells may proliferate excessively, and new stenosis (restenosis) may develop in the lesion area in some cases. Therefore, a drug eluting balloon (DEB) has recently been used in which an outer surface of the balloon is coated with a drug for restraining the stenosis. If the drug eluting balloon is inflated, the drug contained in the coated outer surface is instantaneously released to the lesion area, thereby enabling the drug to be transferred to a biological tissue. In this manner, the restenosis can be restrained.

It has been found that a morphological form of the drug on the coated surface of the balloon obviously influences the drug released to the lesion area from the surface of the balloon in terms of the releasing capability or the tissue transferability of the drug. In this regard, it becomes important to control the crystalline form or the amorphous form of the drug on the coated surface of the balloon.

Various methods have been proposed for coating the balloon with a drug. For example, U.S. Pat. No. 8,597,720 discloses that while the balloon is rotated, a coating solution containing the drug is supplied to the surface of the balloon, and the coating solution is dried to form a coating layer containing the drug.

SUMMARY OF THE INVENTION

Incidentally, the drug on the coated outer surface of the balloon is classified into different morphological forms such as a crystalline form, an amorphous form, and a mixed form of the crystalline and amorphous forms, depending on various conditions such as the length of time needed to volatilize a solvent. Neither the crystalline form nor the amorphous form is necessarily more desirable than the other. It is instead desirable that the morphological form can be selected according to the purpose of the drug.

The balloon coating method, balloon rotating method, and balloon coating device disclosed in this application involve applying a proper quantity of coating solution to an outer surface of a balloon, and involve properly setting/controlling a morphological form of a drug used in coating the balloon.

A balloon coating method for forming a coating layer containing a water-insoluble drug on an outer surface of a balloon of a balloon catheter. The balloon coating method has a step of applying a rotation force at the same rotation speed to both a proximal side and a distal side further from a region where the balloon of the balloon catheter is inflated, moving a dispensing tube for supplying a coating solution containing the drug relatively to the balloon in an axial direction of the balloon while rotating the balloon around an axis of the balloon, so as to apply the coating solution to the outer surface of the balloon.

As described above, the rotation force is applied at the same rotation speed to both the proximal side and the distal side further from the region where the balloon of the balloon catheter is inflated. Accordingly, the balloon is less likely to be twisted or biased. Therefore, a position of the outer surface of the balloon is less likely to vary during the rotation, thereby enabling a proper quantity of coating solution to be applied to the outer surface of the balloon. It also becomes easier to set a desired value for a contact force of the dispensing tube which is kept in contact with the balloon, and it is possible to properly set a morphological form of the drug used in coating the balloon.

The balloon may be rotated while being pulled in the axial direction of the balloon and while the coating solution is applied to the outer surface of the balloon. The deformation (i.e., undesired curvature or bending) of the balloon catheter can thus be corrected by the pulling force. The rotation force can thus be easily applied to the balloon from both the proximal portion and the distal portion of the balloon catheter.

A joint portion of an inner tube penetrating into the balloon and the balloon may be pinched and pulled so as to apply a pulling force to the balloon. The joint portion is thicker than the surrounding portions, and the outer peripheral surface is configured to include the flexible material of the balloon. Accordingly, the pulling force and the rotation force can be effectively applied to the balloon via the joint portion (which is easily pinched and through which the rotation force is easily applied).

An end portion side having an opening portion for discharging the coating solution of the flexible dispensing tube may be brought into contact with the outer surface of the balloon while the balloon is being rotated, so as to face in a direction opposite to a rotation direction of the balloon. The dispensing tube can be simultaneously moved relative to the balloon in the axial direction of the balloon, so that the coating solution is discharged from the opening portion is applied to the outer surface of the balloon. The frictional force between the dispensing tube and the balloon thus increases, thereby causing a condition that the balloon is likely to be twisted or biased. However, the rotation force is applied at the same rotational speed to both the proximal side and the distal side of the balloon. Accordingly, it is possible to adopt a configuration in which the balloon is less likely to be twisted or biased. Therefore, the rotation of the balloon is stabilized while the dispensing tube discharges the coating solution in the direction opposite to the rotation direction of the balloon expedites the crystallization of the water-insoluble drug. Accordingly, it becomes easier to set a desired value for the contact force of the dispensing tube which is kept in contact with the balloon, and it is possible to properly set the morphological form of the drug used in coating the balloon.

Another aspect of the disclosure involves a balloon rotating method for rotating a balloon catheter. The balloon rotating method includes applying a first rotation force to the balloon catheter proximal to the proximal end of the balloon of the balloon catheter at a first rotation speed; applying a second rotation force to the balloon catheter distal to the distal end of the balloon of the balloon catheter, the second rotation force being applied simultaneously while the first rotation force is being applied to the balloon catheter to rotate the balloon about the longitudinal axis of the balloon catheter, the second rotation force being applied at a second rotation speed; and the first rotation speed being the same as the second rotation speed The rotation force is applied at the same rotation speed to both the proximal side and the distal side further from the region where the balloon of the balloon catheter is inflated. Accordingly, the balloon is less likely to be twisted or biased, and the position of the outer surface of the balloon is less likely to vary during the rotation.

The balloon may be rotated while the balloon is pulled in an axial direction of the balloon. The deformation of the balloon is thus corrected by the pulling force. Accordingly, the rotation force can be easily applied to the balloon from both the proximal side and the distal side of the balloon.

A joint portion of an inner tube penetrating into the balloon and the balloon may be pinched and pulled so as to apply a pulling force to the balloon. The joint portion is thicker than the surrounding portions, and the outer peripheral surface is configured to include the flexible material of the balloon. Accordingly, the pulling force and the rotation force can be effectively applied to the balloon via the joint portion which is easily pinched and through which the rotation force is easily applied.

Yet another aspect of the disclosure involves a balloon coating device for forming a coating layer containing a water-insoluble drug on an outer surface of a balloon of a balloon catheter. The balloon coating device includes a first rotary drive unit configured to apply a first rotation force to the balloon catheter. The balloon catheter includes an elongated shaft extending in an axial direction and a balloon connected to the elongated shaft. The balloon is expandable radially outward and deflatable radially inward. The balloon includes a distal end and a proximal end. The first rotary drive unit applies the first rotation force at a first position proximal to the proximal end of the balloon of the balloon catheter at a first rotation speed, and a second rotary drive unit is configured to apply a second rotation force to the balloon catheter at a second position distal to the distal end of balloon. The second rotary drive unit applies the second rotation force at a second rotation speed. The second rotary drive unit is configured to apply the second rotation force while the first rotatory drive unit applies the first rotation force. The first rotation speed applied by the first rotary drive unit is equal to the second rotation speed applied by the second rotary drive unit. The balloon coating device includes a container storing a coating solution containing the water-soluble drug, a movable carriage configured to move in the axial direction, and a dispensing tube connected to the container for applying the coating solution containing the water-soluble drug to the outer surface of the balloon to form the coating layer on the outer surface of the balloon. The dispensing tube is connected to the movable carriage so that movement of the carriage in the axial direction results in movement of the dispensing tube in the axial direction.

The rotation force can be applied at the same rotation speed to both the proximal side and the distal side further from the region where the balloon of the balloon catheter is inflated. Accordingly, the rotating balloon is less likely to be twisted or biased. Therefore, a position of the outer surface of the balloon is less likely to vary during the rotation, thereby enabling a proper quantity of coating solution to be applied to the outer surface of the balloon. In addition, the position of the outer surface of the balloon is less likely to vary during the rotation. Accordingly, it becomes easier to set a desired value for a contact force of the dispensing tube which is kept in contact with the balloon, and it is possible to properly set a morphological form of the drug used in coating the balloon.

The balloon coating device may be configured to further have a pulling unit that applies a pulling force in the axial direction of the balloon while maintaining a state where the balloon is rotatable. In this manner, the deformation of the balloon is corrected by the pulling force. Accordingly, the rotation force can be easily applied to the balloon from both the proximal side and the distal side of the balloon.

BRIEF DESCRIPTION OF THE DRAWINGS

FIGS. 4(A) and 4(B) are plan views illustrating a drive shaft. FIG. 4(A) illustrates a state before the drive shaft interlocks with a three-way stopcock, and FIG. 4(B) illustrates a state where the drive shaft interlocks with the three-way stopcock.

FIG. 5 is a perspective view illustrating a support unit.

DETAILED DESCRIPTION

Figure 1:
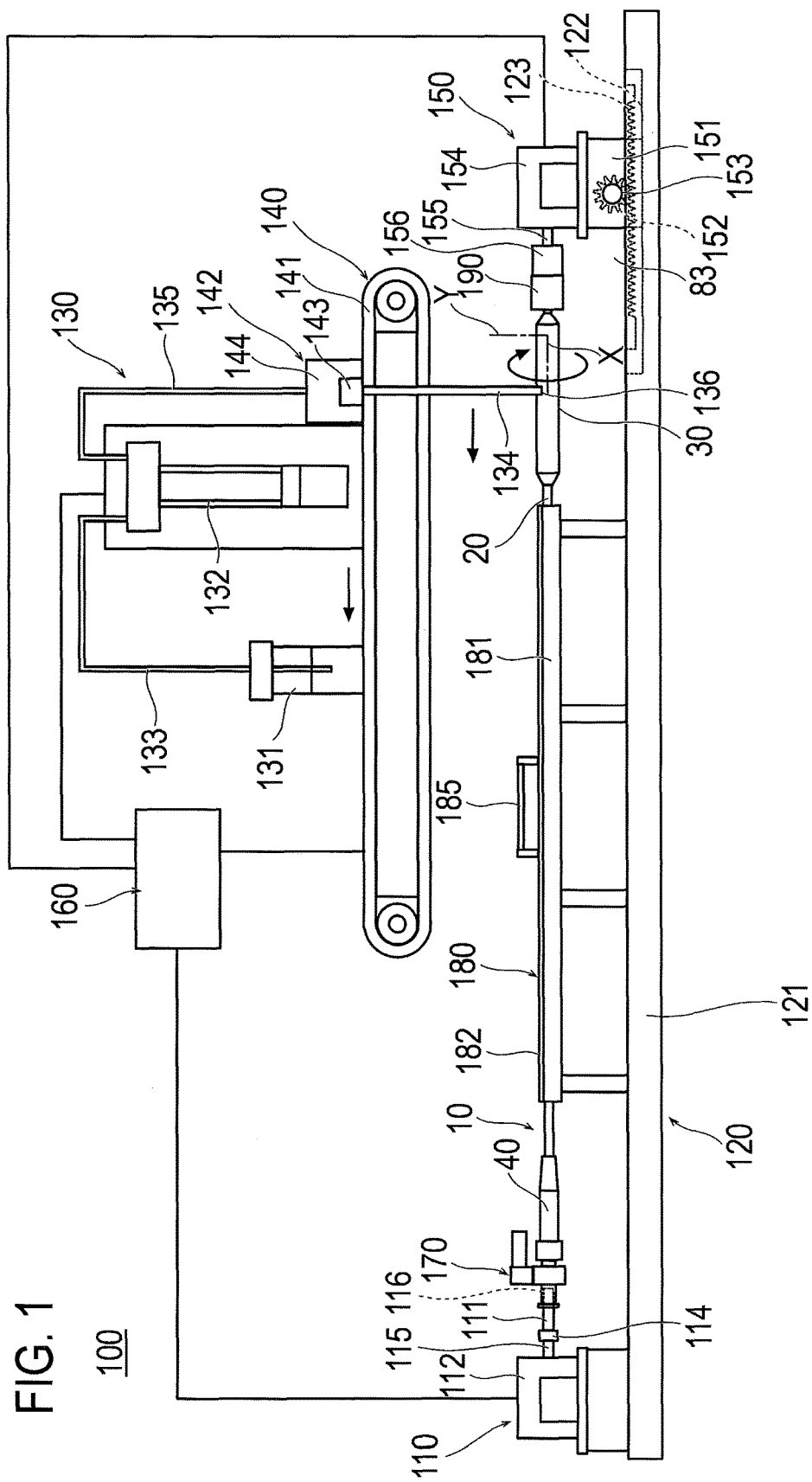
FIG. 1 is a schematic view illustrating a device for carrying out a balloon coating method according to a first embodiment.

Set forth below with reference to the accompanying drawings is a detailed description of embodiments of a balloon coating method, a balloon rotating method and a balloon coating device representing examples of the inventive methods and device disclosed here. In some cases, a dimension ratio in the drawings may be exaggerated and different from a ratio used in practice in order to facilitate the description.

<First Embodiment>

A balloon coating method according to a first embodiment forms a coating layer containing a water-insoluble drug on an outer surface of a balloon. The balloon coating method may be carried out by the balloon coating device 100 illustrated in FIG. 1. In the below description, a side of a balloon catheter 10 which is inserted into a body lumen is referred to as a "distal end" or a "distal side", and an operating hand side (i.e., the side opposite the distal end or distal side in the axial direction of the balloon catheter) is referred to as a "proximal end" of a "proximal side".

Figure 2:
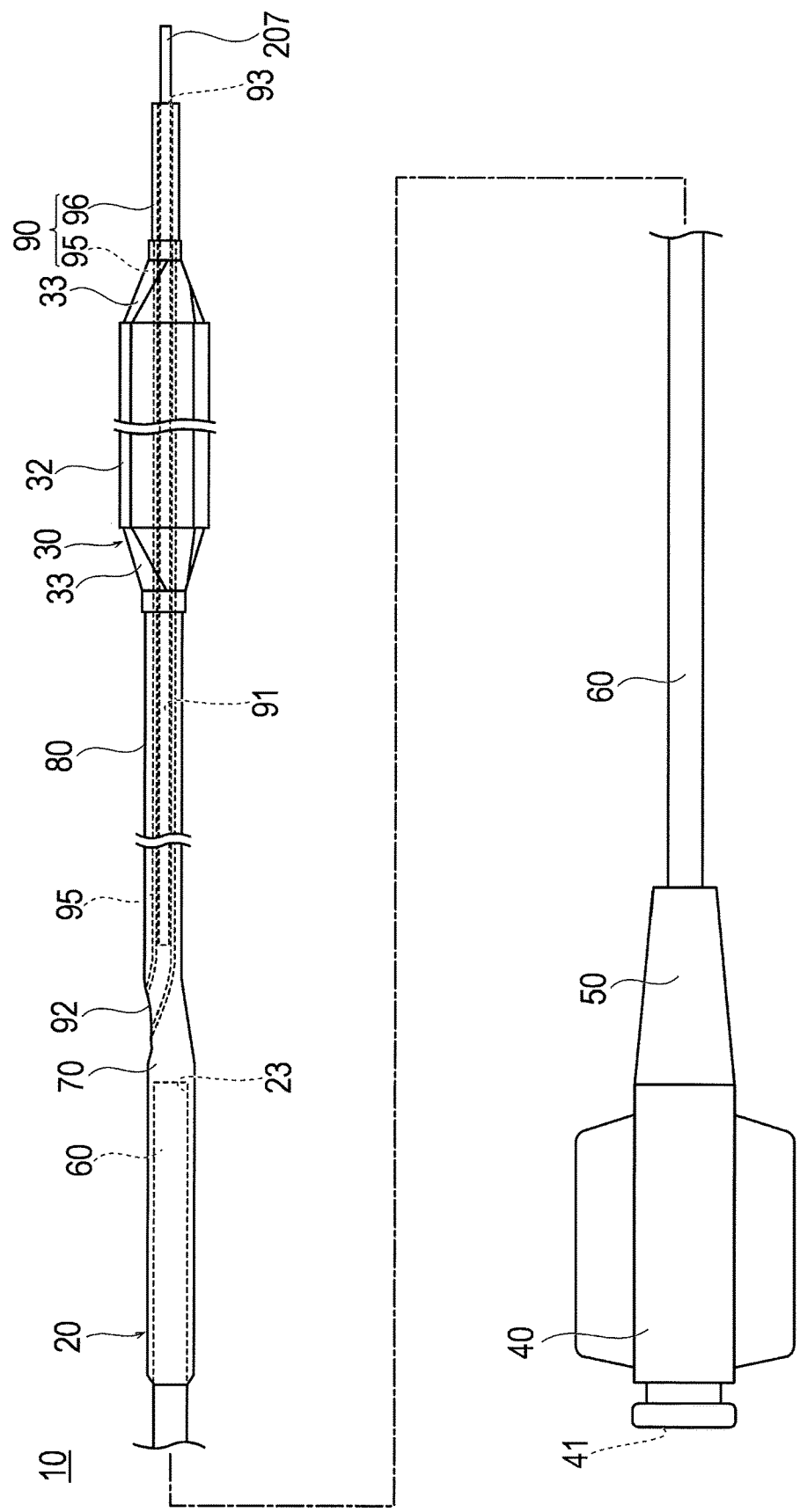
FIG. 2 is a plan view illustrating a balloon catheter.
Figure 3:
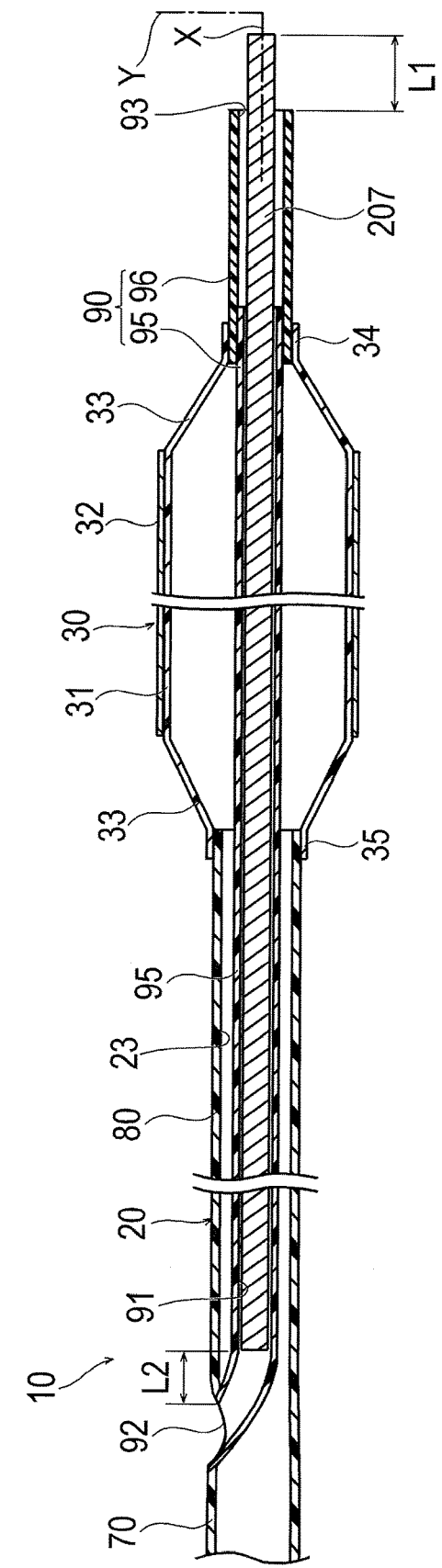
FIG. 3 is a sectional view illustrating a distal portion of the balloon catheter illustrated in FIG. 2.

First, a structure of the balloon catheter 10 will be described. The balloon catheter 10 is a so-called rapid exchange type catheter. As illustrated in FIGS. 2 and 3, the balloon catheter 10 has an elongated catheter shaft 20 (shaft), a balloon 30 disposed in the distal portion of the catheter shaft 20, a hub 40 fixed to the proximal end of the catheter shaft 20, and a kinking resistant tube 50 disposed in a connection section between the catheter shaft 20 and the hub 40.

The catheter shaft 20 includes a tubular proximal shaft 60 whose proximal side is fixedly attached to the hub 40, a tubular intermediate shaft 70 that covers the distal side of the proximal shaft 60, a tubular distal shaft 80 disposed on the distal side of the intermediate shaft 70, and a tubular inner tube 90 inside the distal shaft 80. A dilation lumen 23 for circulating an inflating fluid for inflating the balloon 30 is formed inside the proximal shaft 60, the intermediate shaft 70, and the distal shaft 80.

The inner tube 90 includes an inner tube shaft 95 which coaxially penetrates into the distal shaft 80 and the balloon 30. The inner tube 90 also includes a flexible distal tip 96 which interlocks with the distal portion of the inner tube shaft 95. The distal tip 96 extends in the distal direction from the distal end of the balloon 30 (i.e., distally beyond the distal end of the balloon 30). The distal portion of the balloon 30 is joined to the outer peripheral surface of the proximal portion of the distal tip 96 while maintaining a liquid-tight state. The proximal end of the inner tube shaft 95 is fixedly attached to a portion (side opening formed on a side surface) in the outer circumferential direction of the intermediate shaft 70 while maintaining a liquid-tight state. The proximal opening of the inner tube shaft 95 is exposed outward (i.e., to the outside environment) from the intermediate shaft 70, thereby configuring a proximal opening portion 92. An internal space from the distal end of the inner tube 90 to the proximal opening portion 92 serves as a guide wire lumen 91. A guide wire can be inserted to enter an inlet of a distal opening portion 93 of the distal tip 96 configuring the inner tube 90 and pass through an outlet of the proximal opening portion 92 of the inner tube shaft 95 configuring the inner tube 90. The guide wire is insertable into the inner tube 90 in this manner. The proximal opening portion 92 may be disposed in the proximal shaft 60 or the distal shaft 80 instead of the intermediate shaft 70. The proximal opening portion 92 also may be disposed in a boundary portion between the intermediate shaft 70 and the distal shaft 80.

The material(s) of the distal shaft 80, the inner tube shaft 95, the distal tip 96, and the intermediate shaft 70 is not particularly limited. For example, suitable materials may include polyolefin (for example, polyethylene, polypropylene, polybutene, ethylene-propylene copolymer, ethylene-vinyl acetate copolymer, ionomer, and a mixture of two or more materials), cross-linked polyolefin, or a polymer material such as polyvinyl chloride, polyamide, polyamide elastomer, polyester, polyester elastomer, polyurethane, polyurethane elastomer, fluorine resin, and polyimide, or a mixture of two or more of these materials.

The proximal shaft 60 is preferably configured from a material having relatively high rigidity. For example, suitable metals such as Ni—Ti, brass, SUS, and aluminum, or a resin such as polyimide, vinyl chloride, and polycarbonate may be used.

The hub 40 includes a hub proximal opening portion 41 functioning as a port which communicates with the dilation lumen 23 of the catheter shaft 20. The hub proximal opening portion 41 allows the inflating fluid to flow in and out (i.e., into and out of the dilation lumen 23). The hub 40 is fixed to the proximal shaft 60 while maintaining a liquid-tight state.

The kinking resistant tube 50 is placed outside the proximal shaft 60 (i.e., circumferentially outside to surround the proximal shaft 60) in order to prevent kinking (bending) of the proximal shaft 60 in the vicinity of the distal end of the hub 40.

The balloon 30 can be inflated to widen a stenosed site (i.e., the balloon 30 can be inflated after being positioned at the stenosed site in a deflated state). A tubular portion 31 having the same outer diameter (i.e., a constant outer diameter) when inflated is formed in the central portion in an axial direction X of the balloon 30. A tapered portion 33 whose outer diameter is gradually changed (i.e., the outer diameter is tapered) is formed on both sides of the tubular portion 31 in the axial direction X. The tubular portion 31 and the tapered portions 33 on both sides form a region where the balloon 30 is actually inflated. A coating layer 32 containing a drug is formed on the entire outer surface of the tubular portion 31 (i.e., the coating layer 32 may be applied to the entirety of the outer surface of the tubular portion 31). The range that the coating layer 32 is applied to the balloon 30 is not limited to only the tubular portion 31. For example, at least a portion of the tapered portion 33 may be included in addition to the tubular portion 31. In some embodiments, the coating layer 32 may be formed on only a portion of the tubular portion 31 (i.e., the coating layer 32 may cover less than an entirety of the outer surface of the tubular portion 31).

The distal side further from the tapered portion 33 on the distal side of the balloon 30 (i.e., the portion of the balloon 30 distal to the distal tapered portion 33) is joined to the outer peripheral surface of the distal tip 96 of the inner tube 90 by means of adhesion or fusion while maintaining a liquid-tight state, thereby configuring a distal joint portion 34 (joint portion). The proximal side further from the tapered portion 33 on the proximal side of the balloon 30 (i.e., the portion of the balloon 30 proximal to the proximal tapered portion 33) is joined to the outer peripheral surface of the distal portion of the distal shaft 80 by means of adhesion or fusion while maintaining a liquid-tight state, thereby configuring a proximal joint portion 35. The interior of the balloon 30 communicates with the dilation lumen 23 formed in the catheter shaft 20. The inflating fluid can thus flow into the balloon 30 from the proximal side via the dilation lumen 23. The inflating fluid flows into the balloon 30 to inflate the balloon 30 (i.e., expand the outer surface of the balloon 30 radially outward). The inflating fluid which flows into the balloon 30 can then be discharged to bring the balloon 30 into a folded state (a deflated state). In some embodiments, a joint portion of the distal portion of the balloon 30 may not be at the distal tip 96 of the inner tube 90, but instead may be at the inner tube shaft 95. In addition, the inner tube 90 may be formed from only the inner tube shaft 95 without having the distal tip 96.

The balloon 30 is preferably flexible to some extent and hard to such an extent that the drug can be released from the coating layer 32 on the outer surface of the balloon 30 when the balloon 30 is inflated after reaching the blood vessel or the tissue (i.e., the target site). Specifically, the balloon 30 is configured to include metal or a resin. It is preferable that at least the surface of the balloon 30 having the coating layer 32 is configured to include a resin. For example, the surface of the balloon 30 material can be polyolefin such as polyethylene, polypropylene, polybutene, ethylene-propylene copolymer, ethylene-vinyl acetate copolymer, ionomer, or a mixture of two or more materials, thermoplastic resins such as soft polyvinyl chloride resin, polyamide, polyamide elastomer, polyester, polyester elastomer, polyurethane, and fluororesin, silicone rubber, or latex rubber. Among these materials, polyamides are preferably used. That is, polyamides are used for at least a portion of the outer surface of the inflatable portion of the medical device that is coated with a drug. The outer surface of the inflatable portion that includes polyamides is provided as a smooth surface. Polyamides are not particularly limited as long as the polymer has an amide bond. Examples of acceptable polyamides include a homopolymer such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), and polydodecanolactam (nylon 12), a copolymer such as caprolactam/lauryllactam copolymer (nylon 6/12), caprolactam/aminoundecanoic acid copolymer (nylon 6/11), caprolactam/$\overline{\omega}$-aminononanoic acid copolymer (nylon 6/9), caprolactam/hexamethylene diammonium adipate copolymer (nylon 6/66), a copolymer of adipic acid and metaxylenediamine, or aromatic polyamide such as a copolymer of hexane diamine and m, p-phthalic acid. A base material of the medical device also employs a polyamide elastomer serving as a block copolymer in which nylon 6, nylon 66, nylon 11, and nylon 12 function as a hard segment and polyalkylene glycol, polyether, and aliphatic polyester function as a soft segment. The above-described polyamides may be used alone or in combination of two or more polyamides.

The coating layer 32 is formed on the outer surface of the base material of the balloon 30 directly, or through a pretreatment layer such as a primer layer, by using a coating method (to be described later).

Next, the balloon coating device 100 will be described. As illustrated in FIG. 1, the balloon coating device 100 includes a rotary drive unit 110 (first rotary drive unit) which rotates the balloon 30 around the axis X of the balloon 30, a foundation unit 120 which supports the balloon catheter 10, and an application unit 130 which has a dispensing tube 134 for applying a coating solution to the outer surface of the balloon 30. The balloon coating device 100 also includes a linear movement unit 140 for moving the dispensing tube 134 relative to the balloon 30 (e.g., relative to the outer surface of the balloon), a pulling unit 150 (second rotary drive unit) which applies a pulling force to the balloon 30, and a control unit 160 which controls the balloon coating device 100.

As illustrated in FIGS. 1 and 4(A)-4(B), the rotary drive unit 110 includes a drive shaft 111 which is inserted into a three-way stopcock 170 to be attached to the hub proximal opening portion 41 (e.g., as shown in FIG. 2) of the hub 40 of the balloon catheter 10. The rotary drive unit 110 includes a first motor 112 which rotates the drive shaft 111 and a first shaft coupling 114 which causes the rotary shaft 115 of the first motor 112 and the drive shaft 111 to interlock with each other (i.e., engage with one another to rotate together). The three-way stopcock 170 is attached to the hub 40. The three-way stopcock 170 may then be opened so that the inflating fluid is allowed to flow into the balloon 30, thereby enabling the balloon 30 to be inflated. The three-way stopcock 170 is thereafter closed to maintain the balloon 30 in an inflated state (i.e., the outer surface of the balloon 30 is maintained in the expanded radially outward position with the inflating fluid in the interior of the balloon 30).

The first motor 112 is fixed to a foundation table 121. The drive shaft 111 interlocks with the rotary shaft 115 of the first motor 112 by using the first shaft coupling 114. A male-luer taper (convex luer taper) 116 (which is tapered such that the outer diameter of the male-luer taper 116 decreases in the distal direction) is formed at the distal portion of the drive shaft 111. The male-luer taper 116 is inserted into a female-luer taper (concave luer taper) 171 formed in the three-way stopcock 170. The male-luer taper 116 can be fitted into (i.e., connected to) the female-luer taper 171 using a frictional force (i.e., the inner surface of the female-luer taper 171 contacts the outer surface of the male-luer taper 116 to create a frictional force to hold the male-luer taper 116 within the female-luer taper 171). A taper rate of the male-luer taper 116 and the female-luer taper 171 is stipulated by ISO 594 or JIS (Standardized Commentary Explanation of Medical Equipment), in which the taper rate is stipulated as 6%. A range into which the drive shaft 111 is inserted is within a range of the three-way stopcock 170 (i.e., at least a portion of the drive shaft 111 axially overlaps with at least a portion of the three-way stopcock 170). The drive shaft 111 is thus easily attachable to and detachable from the three-way stopcock 170, thereby improving convenience.

The male-luer taper 116 of the drive shaft 111 may be inserted into and fit to a female-luer taper formed in the hub proximal opening portion 41 of the hub 40 instead of being inserted into and fit to the female-luer taper 171 of the three-way stopcock 170. In this case, the drive shaft 111 is not inserted into the distal side further from the hub 40, thereby the catheter shaft 20 can be flexibly bent, and the drive shaft 111 can be easily attached to and detached from the balloon catheter 10, thereby improving convenience.

The foundation unit 120 includes the foundation table 121. The foundation table 121 serves as a foundation for the balloon coating device. A support unit 180 is fixed to the foundation table 121. The support unit 180 rotatably supports the catheter shaft 20. The foundation unit 120 includes a guide groove portion 122 which holds the pulling unit 150 so that the pulling unit 150 is linearly movable and a rack 123 with linearly aligned teeth.

Figure 6:
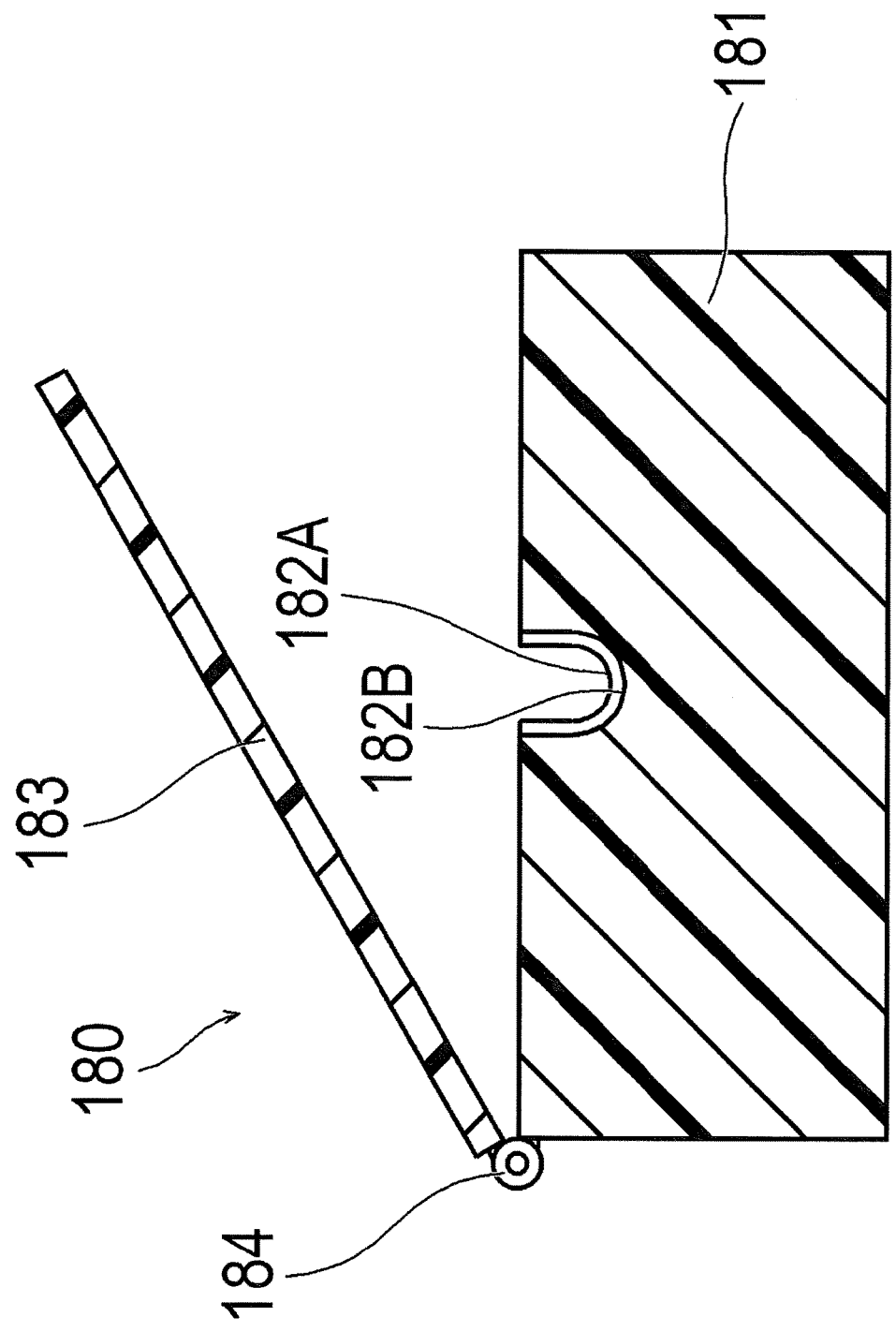
FIG. 6 is a sectional view taken along line VI-VI in FIG. 5.

As illustrated in FIGS. 1, 5, and 6, the support unit 180 includes a support table 181 having a groove portion 182 (groove) for rotatably accommodating the catheter shaft 20 (i.e., the catheter shaft 20 may be positioned within the groove portion 182 and is rotatable while being positioned in the groove portion 182). The support unit 180 also includes a lid portion 183 (lid) which can cover a support surface 186 having the groove portion 182 of the support table 181 (i.e., the groove portion 182 is a groove within the support surface 186 as illustrated in FIG. 5) and a hinge portion 184 which interlocks with the lid portion 183 so that the lid portion 183 is openable and closeable relative to the support table 181. The lid portion 183 has a handle 185 to allow a user to easily grip the lid portion 183 to open and close the lid portion 183.

The support table 181 is elongated in the axial direction X so that the elongated catheter shaft 20 can be supported by the support table 181. The groove portion 182 formed on the support surface 186 includes a first groove portion 182A which supports a portion of the catheter shaft 20 close to the balloon 30, a second groove portion 182B which supports a range of the catheter shaft that includes the proximal opening portion 92, and a third groove portion 182C which supports the catheter shaft 20 proximal to the proximal opening portion 92. The first groove portion 182A, the second groove portion 182B, and the third groove portion 182C are arranged side by side (consecutively) distal to the drive shaft 111 on an extension line of the drive shaft 111 (i.e., coaxial with the drive shaft 111 and/or parallel with the drive shaft 111). The first groove portion 182A, the second groove portion 182B, and the third groove portion 182C may also be slightly displaced downward in the vertical direction from the extension line of the drive shaft 111 to account for deformation caused by the weight of the catheter shaft 20 between the drive shaft 111 and the support table 181. The second groove portion 182B has a larger width and depth than the width and depth of the first groove portion 182A and the third groove portion 182C so that damage due to friction to the proximal opening portion 92 partially protruding from the outer periphery of the catheter shaft 20 can be prevented. The width and the depth of the groove portion formed in the support table 181 may be constant in some embodiments. In addition, any one of the width and the depth of the groove portions 182A, 182B, and 182C formed in the support table 181 may vary depending on the location.

It is preferable that the width and the depth of the groove portion 182 (the first groove portion 182A, the second groove portion 182B, and the third groove portion 182C) are larger than the outer diameter of the catheter shaft 20 by as much as 1 to 5 mm. If the dimensions (width and depth) of the groove portion 182 are too small, the catheter shaft 20 is more likely to be damaged due to friction between the groove portion 182 and the catheter shaft 20. Friction between the groove portion 182 and the catheter shaft 20 also increases the rotation load. Consequently, the balloon 30 may be unstably rotated, and a proper quantity of the coating layer 32 is less likely to be formed. There is also a possibility that a morphological form of the drug may be less likely to be adjusted in the coating layer 32. If the dimensions (width and depth) of the groove portion 182 are too large, however, the catheter shaft 20 may be unmanageably rotated inside the groove portion 182 (i.e., the groove portion 182 does not support the catheter shaft 20), so that the balloon 30 is unstably rotated. Consequently, a proper quantity of the coating layer 32 is less likely to be formed on the outer surface of the balloon 30. There is also a possibility that a morphological form of the drug may be less likely to be adjusted in the coating layer 32.

In the present embodiment, the shape of the bottom surface of the groove portion 182 is semicircular in a cross section orthogonal to the axial direction X. However, the shape of the groove portion 182 is not limited to a semicircular cross-sectional shape. For example, the groove portion 182 may have a V-shape or a rectangular shape. It is preferable that the groove portion 182 has a shape which comes into contact with the catheter shaft 20 so that the catheter shaft 20 is less likely to be damaged. Therefore, it is preferable that the shape of the groove portion 182 has no protruding portion (formed like a W-shape) in a cross section orthogonal to the axial direction X.

The lid portion 183 is pivotably held by the hinge portion 184 and can close the groove portion 182 by covering the support surface 186 (i.e., the lid portion 183 in the closed position provides an upper surface that covers the groove portion 182). The lid portion 183 may be rotated (opened) to be separated from the support surface 186, thereby enabling the groove portion 182 to be exposed. The lid portion 183 serves to maintain the catheter shaft 20 rotating inside the groove portion 182 within a range of the groove portion 182. Preferably, the lid portion 183 possesses a sufficient weight such that the rotating catheter shaft 20 does not jump out (i.e., move out) of the groove portion 182. For example, the lid portion 183 may possess a weight of 30 g or more. The lid portion 183 may have a lock mechanism (not illustrated) for being fixed to the support table 181. For example, the lock mechanism may be a snap fit.

The configuration material(s) of the support table 181 and the lid portion 183 is not particularly limited. For example, a material having a small coefficient of friction such as PTFE (tetrafluoroethylene) and rigid polyethylene may be used.

As illustrated in FIG. 1, the pulling unit 150 (second rotary drive unit) includes a sliding portion 151 which is fitted to the guide groove portion 122 of the foundation unit 120. The pulling unit 150 further includes a pinion 152 which meshes with the rack 123 (i.e., engages with the rack 123), a dial 153 which rotates the pinion 152, and a holding portion 190 which holds the balloon catheter 10. The pulling unit 150 includes a second motor 154 which rotates the holding portion 190 and a second shaft coupling 156 which causes the rotary shaft 155 of the second motor 154 and the holding portion 190 to interlock with each other (i.e., so that the rotary shaft 155 and the holding portion 190 rotate together/integrally rotate).

The sliding portion 151 is slidably fitted to the guide groove portion 122 of the foundation unit 120. The sliding portion 151 is slidable (i.e., configured to slide or to linearly move) inside the guide groove portion 122 to linearly move the second motor 154. The pinion 152 is rotated by rotatably operating the dial 153. The pinion 152 meshes with the rack 123. In this manner, the sliding portion 151 can be moved along the guide groove portion 122. A pulling force (i.e., to pull the balloon 30 in the distal direction) can be applied to the balloon 30 by rotating the dial 153. The amount of the pulling force is not particularly limited. For example, the pulling force is preferably 5 N to 15 N. If the pulling force is too weak, the bending of the balloon 30 cannot be corrected. If the pulling force is too strong, there is a possibility that the balloon 30 may be damaged by the pulling force. If the pulling force is applied to the balloon 30, a force is applied in a direction in which the male-luer taper 116 of the drive shaft 111 may fall out of the female-luer taper 171 of the three-way stopcock 170 (i.e., the pulling force causes the female-luer taper 171 to be pulled away from the male-luer taper 116 in the distal direction). Therefore, it is preferable that the fixing strength of the drive shaft 111 and the three-way stopcock 170 is set to withstand the applied pulling force. For example, the fixing strength may be 10 to 50 N. If the fixing strength of the drive shaft 111 and the three-way stopcock 170 is too strong, however, there is a possibility that the hub 40 may be damaged when the balloon catheter 10 is detached from the device. For example, when the material of the balloon 30 of the balloon catheter 10 is a polyamide-based resin, the outer diameter of the balloon 30 is 6 mm when the balloon 30 is inflated, and the length of the balloon 30 is 150 mm, it is confirmed that the balloon 30 will be damaged if a force of 25 N is applied. If the fixing strength of the drive shaft 111 and the three-way stopcock 170 is too weak, however, the pulling force is applied to the balloon 30, thereby causing a possibility that the drive shaft 111 and the three-way stopcock 170 may no longer interlock with each other.

Instead of manually and rotatably operating the dial 153, the dial 153 can be controlled by providing a motor in some embodiments.

Figure 7:
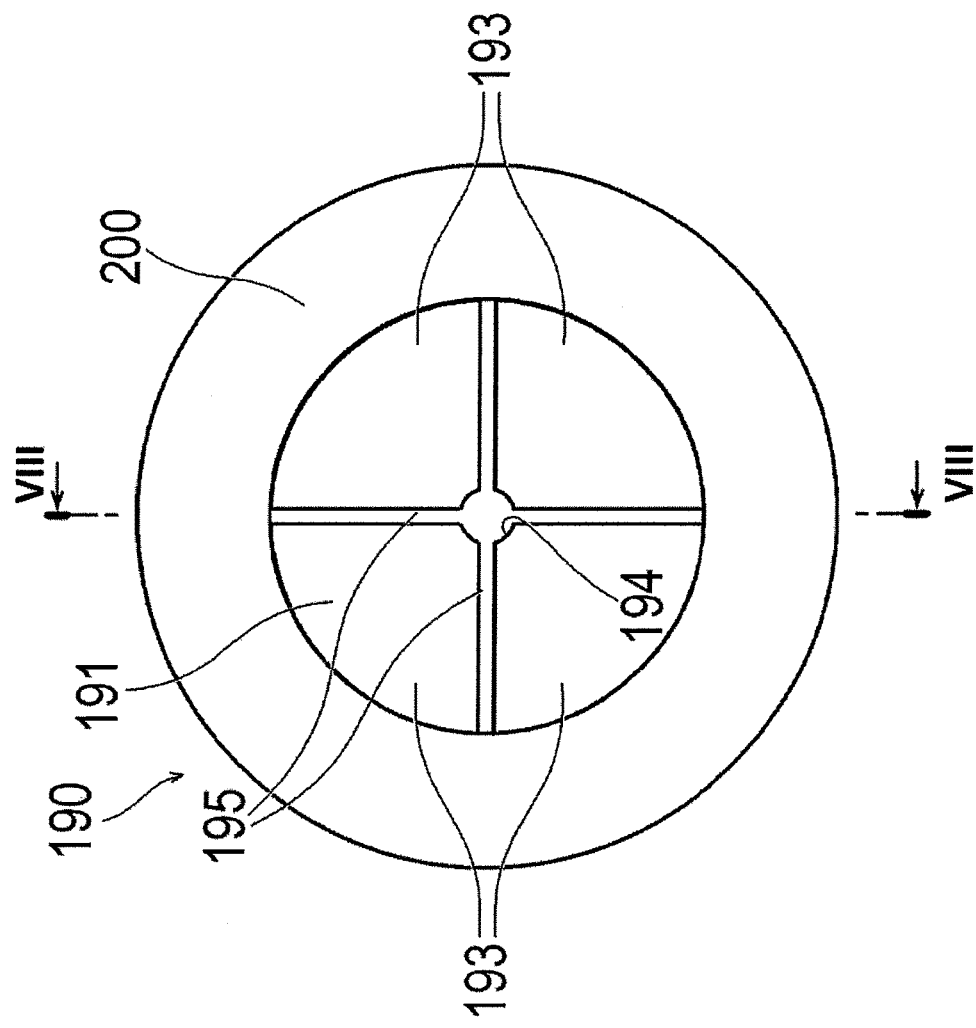
FIG. 7 is a plan view illustrating a holding portion.
Figure 8:
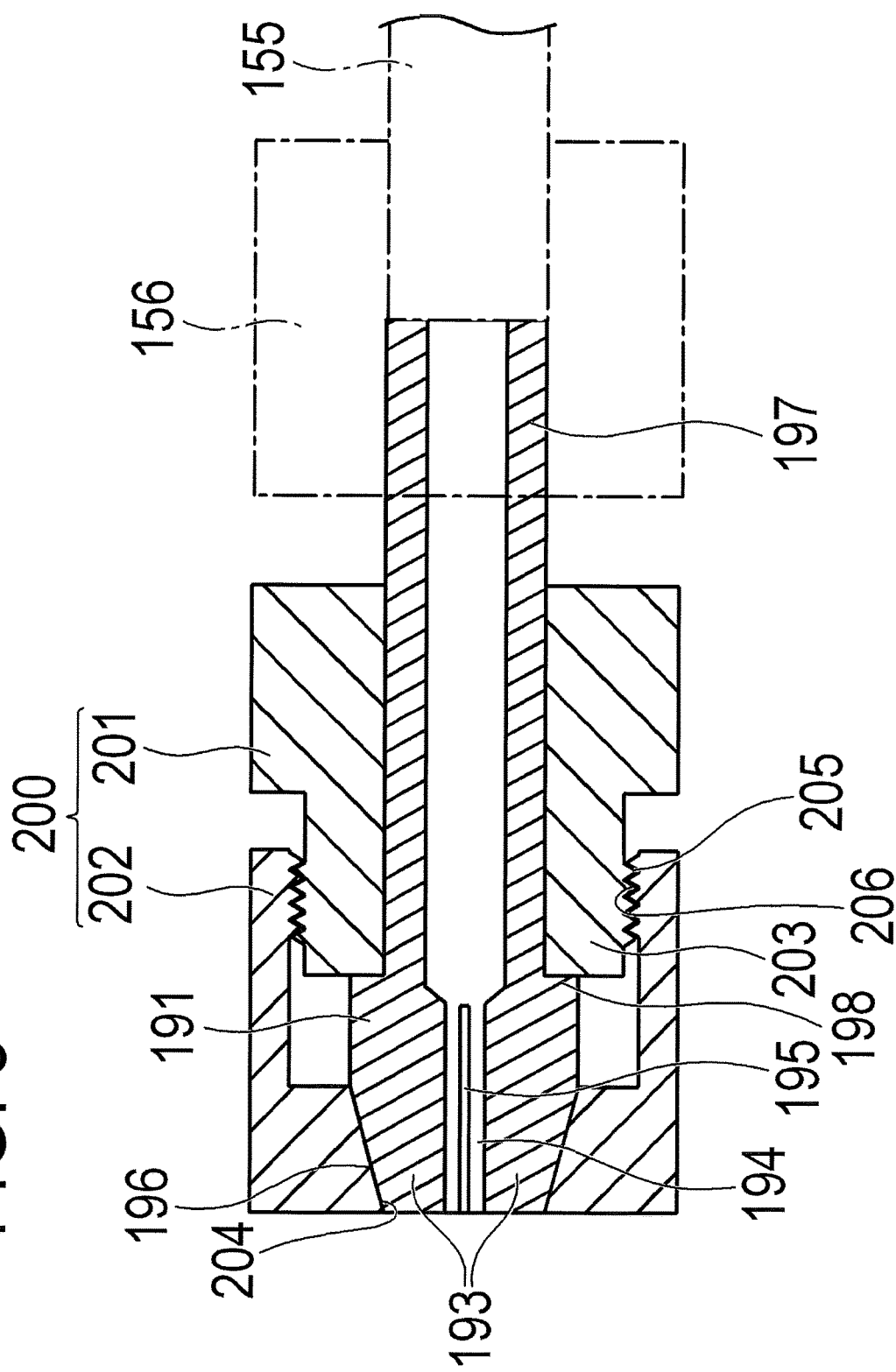
FIG. 8 is a sectional view taken along line VIII-VIII in FIG. 7.

As illustrated in FIGS. 7 and 8, the holding portion 190 includes a collect chuck 191 and a chuck holder 200 which holds the collect chuck 191.

The collect chuck 191 has a slit 195 formed so that a plurality (four in the embodiment illustrated in FIG. 7) of the pinching portions 193 having a pinching surface 194 are aligned in the circumferential direction. The pinching surfaces 194 have a shape corresponding to a shape of a gripping target. The collect chuck 191 has a tapered surface 196 formed on the outer peripheral surface on an end side where the pinching portion 193 is formed as shown in FIG. 8. The collect chuck 191 also has an interlock portion 197 interlocking with the second shaft coupling 156 on a side opposite to the side (in the axial direction) where the pinching portion 193 is formed. The outer diameter of the interlock portion 197 is smaller than the outer diameter of the pinching portion 193. A step portion 198 whose outer diameter decreases is formed between the pinching portion 193 and the interlock portion 197. The pinching surface 194 is formed by a groove-like curved surface extending along the axis of the distal joint portion 34 in which the gripped balloon 30 and the inner tube 90 are coupled to each other. The pinching surface 194 can grip the distal joint portion 34 by using the curved surface so that the distal joint portion 34 is not deformed (if possible). As long as the distal joint portion 34 can be gripped using the curved surface so that the distal joint portion 34 is not deformed (or minimally deformed), a scroll chuck, a drill chuck, or an independent chuck may be used instead of the collect chuck 191. The number of pinching portions 193 is not limited to four and can be any number as long as two or more pinching portions are employed.

The chuck holder 200 includes a first holder 201 through which the interlock portion 197 of the collect chuck 191 penetrates and a second holder 202 that contacts the pinching portion 193 of the collect chuck 191 as illustrated in FIG. 8. The first holder 201 is a tubular member through which the interlock portion 197 of the collect chuck 191 penetrates. One end side of the first holder 201 includes an attachment portion 203 which can contact the step portion 198 so that the step portion 198 of the collect chuck 191 is caught (seated) on the attachment portion 203 as illustrated in FIG. 8. A first screw portion 205 is formed on the outer peripheral surface of the attachment portion 203. The second holder 202 is a tubular member having a second screw portion 206 that is configured to be screwed onto (i.e., threaded into) the first screw portion 205. The inner peripheral surface of the second holder 202 has a tapered pressing surface 204 which contacts the tapered surface 196 of the chuck holder 200. The collect chuck 191 is placed inside the first holder 201, the attachment portion 203 is brought into contact with the step portion 198, and the second screw portion 206 of the second holder 202 is screwed with the first screw portion 205 of the first holder 201. If the second holder 202 is rotated in this way, the second holder 202 moves in a direction closer to the first holder 201. If the second holder 202 moves in the direction closer to the first holder 201, the pressing surface 204 of the second holder 202 slides on the tapered surface 196 of the collect chuck 191, and the pinching portion 193 is deformed so that the slit 195 is narrowed. The pinching surfaces 194 thus move close to each other. This configuration of the holding portion 190 allows the distal portion of the balloon catheter 10 to be pinched at the center of the pinching surfaces 194. It is preferable that a portion of the balloon catheter 10 to be pinched by the pinching portions 193 is the distal joint portion 34 where the balloon 30 of the balloon catheter 10 and the inner tube 90 are joined to each other. However, the pinching location is not limited to the distal joint portion 34 as long as the balloon catheter 10 can be appropriately pinched (i.e., held or secured).

The collect chuck 191 and the chuck holder 200 material(s) may be, for example, a metal such as stainless steel and aluminum or a resin such as a fluororesin, acrylonitrile butadiene styrene resin, and polyethylene.

Figure 9:
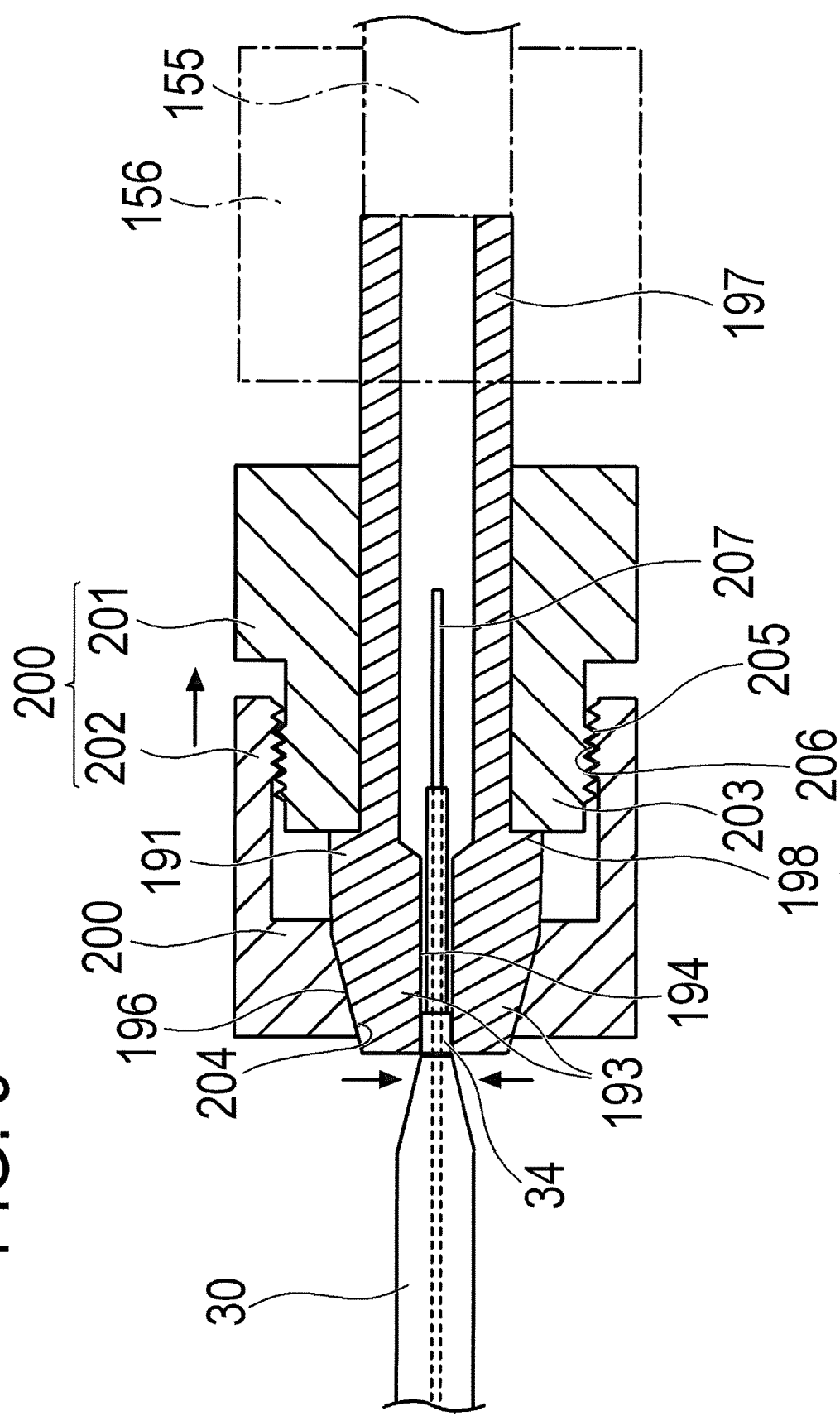
FIG. 9 is a sectional view illustrating a state where the balloon catheter is held by the holding portion.

When the balloon catheter 10 is gripped by the collect chuck 191, the core 207 is placed inside the guide wire lumen 91 as illustrated in FIGS. 3 and 9 so that the balloon catheter 10 does not collapse. The distal portion of the core 207 protrudes distally beyond the distal opening portion 93 of the guide wire lumen 91, and the proximal portion of the core 207 is located proximal to a region where the balloon 30 is inflated as illustrated in FIG. 3. A protrusion length L1 of the core 207 from the distal opening portion 93 is not particularly limited. However, it is preferable that the protrusion length L1 enables the distal portion of the core 207 to reliably protrude beyond the distal opening portion 93 in order to help restrain the collapse of the balloon catheter 10. For example, the protrusion length L1 may be 2 to 50 mm.

As discussed above, the distal portion of the core 207 protrudes distally beyond the distal opening portion 93 of the guide wire lumen 91, and the proximal portion is located proximal to the region where the balloon 30 is inflated. Therefore, the core 207 exists inside the portion of the balloon catheter 10 that is pinched by the pinching portion 193 to help restrain the balloon catheter 10 from being deformed (due to collapse).

The proximal portion of the core 207 does not protrude proximally beyond the proximal opening portion 92 of the guide wire lumen 91. The proximal portion of the core 207 is located in the vicinity (i.e., at substantially the same axial position) of the proximal opening portion 92 or distal to the proximal opening portion 92. The position of the proximal portion of the core 207 is located in the proximal end (balloon fused portion 35) of the balloon inflating portion or the proximal portion of the core 207 is proximally beyond the position of the proximal end (balloon fused portion 35) of the balloon inflating portion. It is preferable that the proximal portion of the core 207 is closer to the proximal opening portion 92. A separated distance L2 between the proximal opening portion 92 and the proximal portion of the core 207 in the distal direction is not particularly limited. For example, the separated distance L2 may be 0 to 50 mm. The proximal portion of the core 207 may be located in the vicinity of the proximal opening portion 92 as long as the proximal portion of the core 207 does not protrude proximally beyond the proximal opening portion 92. Accordingly, even if the balloon catheter 10 is rotated, it is possible to restrain an external member and the core 207 from interfering with each other. It is also possible to adopt a configuration in which the position of the outer surface of the balloon 30 is less likely to vary during the rotation.

If the collapse of the balloon catheter 10 is restrained and the position of the outer surface of the balloon 30 is less likely to vary (i.e., held relatively more steady) during the rotation, it is possible to apply a proper quantity of coating solution (i.e., a more proper quantity than if the collapse of the balloon catheter 10 is not restrained and/or the position of the outer surface of the balloon is more likely to vary) to the outer surface of the balloon 30. Furthermore, it becomes easier to set a desired value for the contact force of the dispensing tube 134 (which is kept in contact with the balloon 30) if the position of the outer surface of the balloon 30 is less likely to vary during the rotation. It is thus possible to more properly set a morphological form of the drug to be used in coating the balloon 30.

It is preferable that a value obtained by subtracting the outer diameter of the core 207 from the inner diameter of the guide wire lumen 91 is equal to or smaller than 0.5 mm, but above zero. If the core 207 is too thick with respect to the inner diameter of the guide wire lumen 91, the inner tube 90 having the guide wire lumen 91 is likely to be damaged by the core 207. If the core 207 is too thin with respect to the inner diameter of the guide wire lumen 91, the inner tube 90 is likely to be deformed when the inner tube 90 is pinched by the pinching portion 93.

The balloon catheter 10 according to the present embodiment is a rapid exchange type. Accordingly, the guide wire lumen 91 does not exist up to the hub 40, and the core 207 does not extend into the hub 40.

As illustrated in FIG. 1, the linear movement unit 140 includes a movable carriage 141 which is linearly movable in a direction parallel to the axis X of the balloon 30. The linear movement unit 140 also includes a tube positioning portion 142 which is placed on the movable carriage 141 to move the dispensing tube 134 in a Y-axial direction and a Z-axial direction which are orthogonal to the axis X (refer to FIG. 10). The movable carriage 141 is linearly movable by a drive source such as a built-in motor. The application unit 130 is placed on the movable carriage 141, so that movement of the movable carriage 141 in both directions along the axis X of the balloon catheter 10 causes the application unit 130 to correspondingly linearly move in both directions along the axis X of the balloon catheter 10. The tube positioning portion 142 includes a tube fixing portion 143 to which the dispensing tube 134 is fixed, and a drive unit 144 which moves the tube fixing portion 143 (and thus the dispensing tube 134) in the Y-axial direction and the Z-axial direction. For example, the drive unit 144 includes a biaxial slider structure that can be moved by a drive source such as a built-in motor or cylinder, thereby enabling the tube fixing portion 143 to move in both the Y-axial direction and the Z-axial direction. The Y-axial direction and the Z-axial direction in which the dispensing tube 134 moves on a plane orthogonal to the axis X of the balloon catheter 10 are not necessarily defined as the vertical direction and the horizontal direction.

The application unit 130 includes a container 131 which contains the coating solution, a liquid feeding pump 132 which feeds the coating solution at any desired feeding rate, and a dispensing tube 134 which applies the coating solution to the outer surface of the balloon 30.

For example, the liquid feeding pump 132 can be a syringe pump. The liquid feeding pump 132 can be controlled by the control unit 160 to aspirate (i.e., suction) the coating solution from the container 131 via an aspiration tube 133. The liquid feeding pump 132 can supply the coating solution to the dispensing tube 134 via the supply tube 135 at any desired feeding rate. The liquid feeding pump 132 is installed in the movable carriage 141, and is linearly movable by the movement of the movable carriage 141 (i.e., linear movement of the movable carriage 141 causes the feeding pump 132 to correspondingly linearly move). The liquid feeding pump 132 is not limited to being a syringe pump as long as the coating solution can be fed by the liquid feeding pump 132 (i.e., pumped from the container 131 to the dispensing tube 134). For example, a tube pump may be used.

Figure 10:
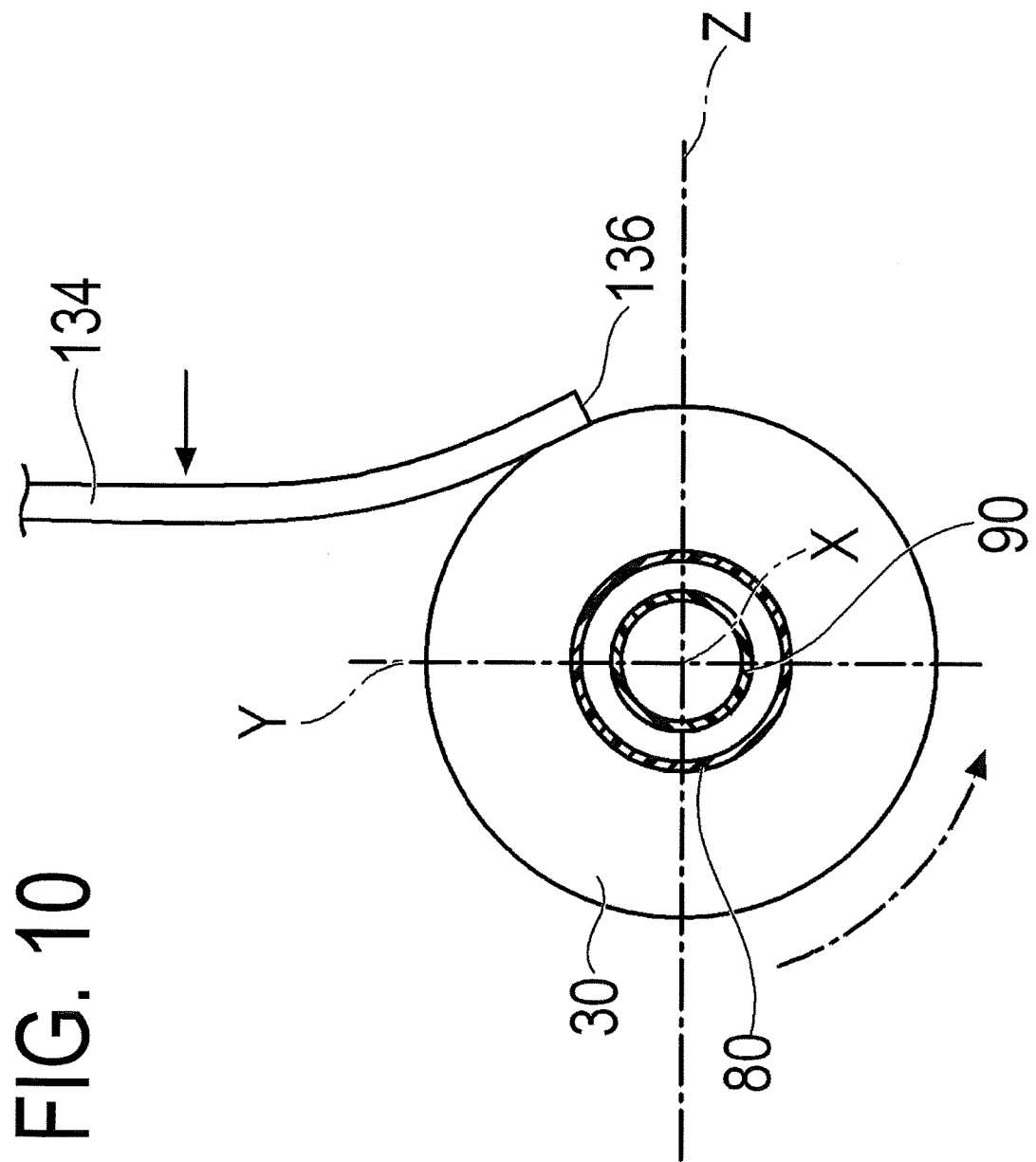
FIG. 10 is a sectional view illustrating a balloon when an outer surface of the balloon is coated with a coating solution.

The dispensing tube 134 is a member which communicates with the supply tube 135 and discharges the coating solution supplied from the liquid feeding pump 132 (via the supply tube 135) to the outer surface of the balloon 30. The dispensing tube 134 is a flexible tubular member. The upper end (i.e., in the vertical direction) of the dispensing tube 134 is fixed to the tube fixing portion 143. The dispensing tube 134 extends downward in the vertical direction from the tube fixing portion 143. The dispensing tube 134 includes an opening portion in a discharge end 136 located in the lower end of the dispensing tube 134 (i.e., the lower end of the dispensing tube 134 is an open end for discharging the coating solution). The opening portion formed in the discharge end 136 of the dispensing tube 134 is formed substantially perpendicular to the axis of the dispensing tube 134. The dispensing tube 134 to linearly move in both directions along the axial direction X of the balloon catheter 10 together with the liquid feeding pump 132 installed in the movable carriage 141 when the movable carriage 141 moves linearly in either direction along the axial direction X. As illustrated in FIG. 10, the dispensing tube 134 is movable by the drive unit 144 in two different directions (in the present embodiment, the Y-axial direction, which is the vertical direction, and the Z-axial direction, which is the horizontal direction) on a plane orthogonal to the axial direction X. A portion of the side surface (i.e., outer peripheral surface) on the discharge end side 136 of the dispensing tube 134 (a portion having a continuous length in the extending direction of the dispensing tube 134) is positioned to directly contact the outer surface of the balloon 30 as illustrated in FIG. 10. The dispensing tube 134 can supply the coating solution to the outer surface of the balloon 30 while the dispensing tube 134 is deflected by being pressed against the outer surface of the balloon 30. Alternatively, the end side of the distal end of the dispensing tube 134 may be pre-shaped and bent so as to form a certain angle relative to the long axis of the dispensing tube 134 (i.e., the longitudinal axis of the dispensing tube 134) and a side surface or at least a portion of the distal end of the bent dispensing tube 134 may be disposed to contact the outer surface of the balloon 30.

The dispensing tube 134 does not need to have a circular tube shape as long as the coating solution can be supplied. In addition, the dispensing tube 134 may not extend in the vertical direction as long as the coating solution can be discharged.

It is preferable that the dispensing tube 134 is formed of a flexible material so that the contact load applied to the balloon 30 can be reduced and a change in the contact position (which is caused by the rotation of the balloon 30) can be absorbed by deformation of the dispensing tube 134. For example, the dispensing tube 134 can be polyolefin such as polyethylene and polypropylene, or fluorine-based resin such as cyclic polyolefin, polyester, polyamide, polyurethane, polytetrafluoroethylene (PTFE), tetrafluoroethylene ethylene copolymer (ETFE), tetra fluoroethylene perfluoroalkylvinylether copolymer (PFA), and tetrafluoroethylene hexafluoropropylene copolymer (FEP). As long as the dispensing tube 134 is flexible and deformable, however, the configuration material is not particularly limited.

The outer diameter of the dispensing tube 134 is not particularly limited. For example, the outer diameter of the dispensing tube 134 can be 0.1 mm to 5.0 mm, preferably 0.15 mm to 3.0 mm, and more preferably 0.3 mm to 2.5 mm. The inner diameter of the dispensing tube 134 is not particularly limited. For example, the inner diameter of the dispensing tube 134 can be 0.05 mm to 3.0 mm, preferably 0.1 mm to 2.0 mm, and more preferably 0.15 mm to 1.5 mm. The length of the dispensing tube 134 is not particularly limited. It is preferable that the length is five (5) times or smaller than the outer diameter of the balloon. For example, the length of the dispensing tube 134 can be 1.0 mm to 50 mm, preferably 3 mm to 40 mm, and more preferably 5 mm to 35 mm.

For example, the control unit 160 is configured to include a computer. The control unit 160 may comprehensively control the rotary drive unit 110, the linear movement unit 140, the pulling unit 150, and the application unit 130. The control unit 160 can synchronously rotate the first motor 112 of the rotary drive unit 110 and the second motor 154 of the pulling unit 150 at the same rotation speed. In addition, the control unit 160 can comprehensively control the rotation speed of the balloon 30, the initial positioning of the dispensing tube 134 with respect to the balloon 30, the moving speed of the dispensing tube 134 relative to the balloon 30 in the axial direction X, and the drug discharge speed from the dispensing tube 134.

The coating solution contains the water-insoluble drug and the solvent. After the coating solution is supplied to the outer surface of the balloon 30, the solvent is volatilized to form the coating layer 32 having a crystalline layer and an amorphous layer on the outer surface of the balloon 30. The balloon 30 and the coating layer 32 can be used as the drug eluting balloon which gradually elutes the drug inside the living body (e.g., at a stenosis site in the living body).

A water-insoluble drug is insoluble or slightly soluble in water. Specifically, the solubility in water is less than 5 mg/mL at pH 5 to 8. The solubility may be less than 1 mg/mL, and further, may be less than 0.1 mg/mL. The water-insoluble drug contains a fat-soluble drug.

Some examples of preferable water-insoluble drugs include immunosuppressants. For example, the water-insoluble drugs include cyclosporins containing cyclosporine, immunostimulants such as rapamycin, anticancer agents such as paclitaxel, antiviral agents, or antimicrobial agents, antineoplastic tissues agents, analgesics, anti-inflammatory agents, antibiotics, antiepileptics, anxiolytics, antialgics, antagonists, neuron blocking agents, anticholinergic agents, cholinergic agents, antimuscarinic agents, and muscarinic agents, antiadrenergic action agents, antiarrhythmic agents, antihypertensive agents, hormonal agents, and nutritional agents.

The water-insoluble drug is preferably at least one selected from a group including rapamycin, paclitaxel, docetaxel, and everolimus. This group of rapamycin, paclitaxel, docetaxel, and everolimus includes analogs of these drugs and/or derivatives of these drugs as long as the resulting drug has similar pharmacological effects. For example, paclitaxel and docetaxel are in an analogous relationship. Rapamycin and everolimus are in a derivative relationship. Paclitaxel is the most preferable of these drugs.

The water-insoluble drug may further contain excipients. Excipients are not limited as long as the drugs are pharmaceutically acceptable. For example, excipients include water soluble polymers, sugars, contrast agents, citric acid esters, amino acid esters, glycerol esters of short chain monocarboxylic acids, or pharmaceutically acceptable salts and surfactants.

It is preferable that a small amount of the excipients is used for the water-insoluble drug. It is also preferable that a matrix is not formed. The excipients preferably do not contain micelles, liposomes, contrast agents, emulsifiers, and surfactants. However, all of these non-preferred embodiments may be included in the excipients. In addition, it is preferable that excipients contain only low molecular compounds without containing polymers.

The solvent is not particularly limited. Solvent examples include tetrahydrofuran, ethanol, glycerin (also referred to as glycerol or propane-1, 2, 3-triol), acetone, methanol, dichloromethane, hexane, ethyl acetate, and water. Among these materials, a mixed solvent of some of tetrahydrofuran, ethanol, acetone, and water is preferably used.

Next, a balloon coating method for forming the coating layer 32 containing the water-insoluble drug on the surface of the balloon 30 will be described with reference to the above-described balloon coating device 100, which is illustrated in FIG. 1.

First, the three-way stopcock 170 interlocks with the hub proximal opening portion 41 of the hub 40 of the balloon catheter 10, and the three-way stopcock 170 is opened (i.e., an operator causes the three-way stopcock 170 to interlock/engage with the hub proximal opening portion 41 of the hub 40 of the balloon catheter 10 and then opens the three-way stopcock 170). A syringe is used to cause inflating fluid to flow into the balloon 30. After the balloon 30 is inflated in this way (i.e., with the injection of the inflating fluid), the three-way stopcock 170 is closed to maintain a state where the balloon 30 is inflated. It is also possible to form the coating layer 32 on the surface of the balloon 30 without inflating the balloon 30. In this case, it is not necessary to supply the inflating fluid into the balloon 30.

Next, the lid portion 183 of the support table 181 is opened. The catheter shaft 20 is accommodated inside (i.e., positioned within) the groove portion 182, and the lid portion 183 is closed. The proximal opening portion 92 of the catheter shaft 20 is accommodated in the second groove portion 182B whose width and depth are larger than the width and depth of the first groove portion 182A and the width and depth of the third groove portion 182C.

Next, the male-luer taper 116 of the drive shaft 111 is inserted into and interlocks with the female-luer taper 171 of the three-way stopcock 170. The rotation force can thus be applied (transmitted) from the first motor 112 to the proximal portion of the balloon catheter 10.

The distal joint portion 34 is then inserted into the pinching portion 193 while the pinching portion 193 of the collect chuck 191 is widely opened (i.e., the pinching portion 193 of the collect chuck 191 is opened to create a space larger than the outer diameter of the distal joint portion 34 of the balloon catheter 10). The pinching portion 193 is deformed to close towards the center (i.e., the inner diameter of the pinching portion 193 decreases/narrows) when the second holder 202 is rotated with respect to the first holder 201. Specifically, when the second holder 202 is rotated with respect to the first holder 201, the second holder 202 moves closer to (in the direction toward) the first holder 201, and the pressing surface 204 of the second holder 202 slides on the tapered surface 196 of the collect chuck 191, thereby deforming the pinching portion 193 so as to move toward the center. The pinching surfaces 194 thus move toward one another to pinch the distal joint portion 34 of the balloon catheter 10. The rotation force can be applied (transmitted) from the second motor 154 to the distal portion of the balloon catheter 10 by the pinching surfaces 194 closing on/pinching the distal joint portion 34 of the balloon catheter 10.

The order of installing (or connecting/positioning) the balloon catheter 10 in the drive shaft 111, the collect chuck 191, and the support table 181 is not particularly limited.

A pulling force is next applied to the balloon 30 by rotation of the dial 153, which causes the second motor 154 and the collect chuck 191 to move in the distal direction. The pulling force applied to the balloon catheter 10 can help correct the curvature of the balloon 30.

Next, the dispensing tube 134 is positioned with respect to the balloon 30. First, the position of the movable carriage 141 is adjusted so that the dispensing tube 134 is appropriately positioned in the axial direction X. In one embodiment, the dispensing tube 134 is first positioned at the utmost distal side position for forming the coating layer 32 in the balloon 30.

The drive unit 144 is then operated to move the dispensing tube 134 and bring the outer peripheral surface of the dispensing tube 134 into contact with the outer surface of the balloon 30 as illustrated in FIG. 10. The balloon 30 is rotated in a direction opposite to the discharge direction of the coating solution discharged from the dispensing tube 134 at the position where the dispensing tube 134 is brought into contact with the balloon 30.

The dispensing tube 134 approaches the outer surface of the balloon 30, and is deformed (i.e., elastically bent) by being pressed against the balloon 30, or the dispensing tube 134 contacts the outer surface of the balloon 30 without being deformed (i.e., elastically bent) by being pressed against the balloon 30. In both cases, the dispensing tube 134 is disposed so that a side surface (outer peripheral surface) on the end portion side of the dispensing tube 134 comes into contact with the surface of the balloon 30.

Next, the coating solution is supplied to the dispensing tube 134 while the liquid feeding amount is adjusted by the liquid feeding pump 132. The balloon catheter 10 is rotated by applying a drive force to both the proximal portion and the distal portion of the balloon catheter 10 by the first motor 112 and the second motor 154, respectively. The movable carriage 141 is then moved to gradually move the dispensing tube 134 in the proximal direction along the axial direction X. The coating solution discharged from the opening portion (i.e., the open end) of the dispensing tube 134 is spirally applied to the outer peripheral surface of the balloon 30 by moving the dispensing tube 134 relative to the balloon 30. The coating solution is thus applied at a position where the balloon 30 is rotated in the direction opposite to the dispensing direction of the dispensing tube 134 (upward direction in the present embodiment) of the outer surface of the balloon 30 (i.e., the dispensing direction is opposite to the balloon 30 rotation direction as shown in FIG. 10). The portion of the outer surface of the balloon 30 to which the coating solution is applied may come into contact with other members (for example, the dispensing tube 134 whose discharge direction is the direction opposite to the rotation direction). When the dispensing tube 134 is gently (slowly) moved along the axial direction of the balloon catheter, the distal end of the dispensing tube 134 comes into contact with substantially the same position in the axial direction of the balloon surface to which the coating solution is applied. As a result, the dispensing tube 134 comes into contact with the location to which the coating solution is applied multiple times and generates crystalline nucleus (seed crystal) in the coating solution on the balloon surface. By coating the outer surface of the balloon 30 and moving the dispensing tube in this manner, a rate of crystallization can be accelerated, and the crystallization can be stabilized. In addition, the dispensing tube 134 whose discharge direction is the same direction as the rotation direction does not come into contact with the location to which the coating solution is applied. In this manner, it is possible to help prevent a possibility of inhibiting the generation of "a morphological form including a plurality of elongated bodies in which the crystal of the water-insoluble drug has each independent long axis", and it is possible to help prevent a possibility that the morphological form may be destroyed after generated. That is, it is preferable that the dispensing tube 134 avoid contacting the outer surface of the balloon 30 to avoid the crystal from being destroyed after the crystal is formed on the balloon surface.

The moving speed of the dispensing tube 134 is not particularly limited. For example, the dispensing tube 134 can have a moving speed of 0.01 to 2 mm/sec, preferably 0.03 to 1.5 mm/sec, and more preferably 0.05 to 1.0 mm/sec. The discharge rate of the coating solution discharged from the dispensing tube 134 is not particularly limited. For example, the discharge rate of the coating solution can be 0.01 to 1.5 µL/sec, preferably 0.01 to 1.0 µL/sec, and more preferably 0.03 to 0.8 µL/sec. The rotation speed of the balloon 30 is not particularly limited. For example, the rotation speed of the balloon 30 can be 10 to 300 rpm, preferably 30 to 250 rpm, and more preferably 50 to 200 rpm. The first motor 112 and the second motor 154 are synchronously rotatable within these ranges of the rotation speed. The diameter of the balloon 30 when applying the coating solution is not particularly limited. For example, the balloon 30 diameter when the coating solution is being applied can be 1 to 10 mm, and preferably 2 to 7 mm.

If the balloon catheter 10 is rotated, a main body portion of the balloon catheter 10 is rotated inside the groove portion 182 of the support table 181. The proximal opening portion 92 partially protruding from the periphery in the catheter shaft 20 is accommodated in the second groove portion 182B (whose width and depth are formed to be larger than the width and depth of the first groove portion 182A and the third groove portion 182C), so that the proximal opening portion 92 can be prevented from being damaged due to friction generated between the proximal opening portion 92 and the second groove portion 182B. The groove portion 182 is covered with the lid portion 183 when the balloon catheter 10 is rotated. Accordingly, it is possible to restrain the catheter shaft 20 from jumping out (falling out) of the groove portion 182, and the balloon 30 can be stably rotated.

If the balloon catheter 10 is rotated, the balloon 30 may be biased due to the curvature along the axial direction X of the balloon 30 in some cases. The dispensing tube 134 is flexible, however, so that even if the balloon 30 is biased, the dispensing tube 134 moves to follow the outer surface of the balloon 30 to maintain a satisfactory contact state between the dispensing tube 34 and the outer surface of the balloon 30. In this manner, it is possible to restrain fluctuations in the thickness of the applied coating solution, thereby easily adjusting the thickness of the morphological form of the coating layer 32.

The solvent contained in the coating solution applied to the surface of the balloon 30 is then volatilized, and the coating layer 32 containing the water-insoluble drug is formed on the surface of the balloon 30. The time for volatilization is appropriately set depending on the solvent. For example, approximately several seconds to several hundred seconds are required.

The amount of the drug in the coating layer 32 is not particularly limited. However, the density is preferably 0.1 µg/mm$^2$ to 10 µg/mm$^2$, preferably 0.5 µg/mm$^2$ to 5 µg/mm$^2$, more preferably 0.5 µg/mm$^2$ to 4 µg/mm$^2$, and the density is most preferably 1.0 µg/mm$^2$ to 3.5 µg/mm$^2$.

The extending direction (discharge direction) of the dispensing tube 134 extending toward the discharge end 136 is the direction opposite to the rotation direction of the balloon 30. Accordingly, the water-insoluble drug of the coating layer 32 formed on the outer surface of the balloon 30 is formed to contain the morphological form including the plurality of elongated bodies in which the crystal of the water-insoluble drug each has an independent long axis.

In the coating layer 32 having the morphological form including the plurality of elongated bodies (in which the crystal of the water-insoluble drug each has an independent long axis), the plurality of elongated bodies in a form in which each crystal has an independently elongated body shape are included in a base material (the outer surface of the balloon 30). The plurality of elongated bodies may extend outward in substantially the circumferential direction with respect to the balloon surface or may be disposed in a direction parallel to the substantially circumferential direction. The plurality of elongated bodies may be combined with each other or may be in contact with each other in a state where different angles are formed by the plurality of adjacent elongated bodies. The plurality of elongated bodies may be located on the balloon surface with a space (i.e., a space having no crystal) between adjacent elongated bodies (i.e., the plurality of elongated bodies are spaced apart from one another on the outer surface of the balloon 30). The preferable coating layer is a layer in which the plurality of elongated bodies containing the crystal of the water-insoluble drug and having the long axis exist in a brush shape. Specifically, the plurality of elongated bodies are circumferentially arranged in a brush shape on the surface of the base material. Each of the elongated bodies independently exists (i.e., the elongated bodies are spaced apart from one another such that each elongated body possesses an independent longitudinal axis) and has a certain length. One end (proximal end) of the length portion of each of the elongated bodies is fixed to the surface of the base material. The elongated body does not form a complex structure with the adjacent elongated body—both of these do not interlock with each other. The long (longitudinal) axis of the crystal is substantially linear. The elongated bodies form a predetermined angle with respect to the surface of the base material where the long axes intersect each other. The predetermined angle is within a range of 45 degrees to 135 degrees. Preferably, the predetermined angle is in a range from 70 degrees to 110 degrees. More preferably, the predetermined angle is in a range from 80 degrees to 100 degrees. Most preferably, the long axes of the elongated bodies form an angle of approximately 90 degrees with respect to the surface of base material. At least the vicinity of the distal end of the elongated body is hollow. The cross section of the elongated body (on a plane vertical (perpendicular) to the long axis of the elongated body) is hollow. The hollow elongated body has a polygonal cross section of the elongated body (on a plane vertical (perpendicular) to the long axis). For example, the polygon can be a quadrangle, a pentagon, or a hexagon. Accordingly, the elongate body has the distal end (or the distal surface) and the proximal end (or the proximal surface), and is formed as an elongated polyhedron in which a side surface between the distal end (or the distal surface) and the proximal end (or the proximal surface) is configured to include a plurality of substantial planes. This crystalline morphological form (hollow elongated body crystalline morphological form) entirely or at least partially configures a certain plane on the surface of the base material.

The features of the layer having the morphological form including the hollow elongated body crystal are as follows.

(1) There are provided the plurality of elongated bodies (rod-shaped bodies) that are each hollow and each have an independent long (longitudinal) axis. The elongated body has a rod shape.

(2) There is provided the elongated body having the long axis, and the cross section of the elongated body on the plane perpendicular to the long axis is the polyhedron having the polygonal shape in many cases. Fifty percent (50%) by volume or more of the elongated body crystal are elongated polyhedrons. The side surface of the polyhedron is predominantly a tetrahedron. In some cases, the elongated polyhedron has a plurality of surfaces (grooves) which are formed at each reentrant angle and whose respective apexes extend in the direction of the long axis of the elongated body. The term "reentrant angle" means that at least one of the interior angles of the polygon of the cross section of the elongated body (on the plane perpendicular to the long axis) is an angle larger than 180 degrees.

(3) In many cases, the elongated body is an elongated polyhedron. That is, when viewed in cross section perpendicular to the long axis of the elongated body, the cross section is the polygon (and is observed, e.g., as a quadrangle, a pentagon, or a hexagon).

(4) The plurality of elongated bodies are aligned on the surface of the base material at an angle where the long axis of each of the elongated bodies is within a predetermined range, preferably in a range of 45 degrees to 135 degrees, relative to the base material. That is, the plurality of elongated bodies each possess an independent long axis that is substantially uniformly erected on the surface of the base material. The erected region is substantially uniformly formed while extending in the circumferential direction and the axial direction on the surface of the base material. The angles of the respective independent elongated bodies with respect to the surface of the base material may be different from each other in a predetermined range, or the angles of the respective independent elongated bodies with respect to the surface of the base material may be the same as each other.

(5) One end (proximal end) of the length portion of each of the elongated bodies is fixed to the surface of the base material.

(6) In some cases, a form of a portion close to the surface of the base material shows a case where particulate, short rod-shaped, or short curved crystals are stacked one on another. In the elongated body having the long axis, there exists an elongated body directly or indirectly having the long axis on the surface of the base material.

Therefore, in some cases, the elongated body having the long axis is erected on a stacked layer.

(7) The length in the axial direction of the elongated body is preferably 5 μm to 20 μm, more preferably 9 μm to 11 μm, and most preferably approximately 10 μm. The diameter of the elongated body is preferably 0.01 μm to 5 μm, more preferably 0.05 μm to 4 μm, and much more preferably 0.1 μm to 3 μm.

(8) Other morphological forms (for example, amorphous plate-like morphological forms) are not mixed on the surface of the layer containing hollow elongated body crystalline morphological form, and 50 volume % or more as the crystalline form, more preferably, 70 volume % or more configure the crystalline morphological form of the above (1) to (7). More preferably, almost all configure the crystalline morphological form of (7).

(9) In the hollow elongated crystalline morphological form, there is a possibility that other compounds may exist in the coating layer containing the water-insoluble drug configuring the crystal. In that case, the compounds exist while being distributed in the space between the crystals (elongated bodies) of the plurality of the water-insoluble drugs which are erected on the surface of the base material of the balloon. In proportion to the substances configuring the coating layer, the crystal of the water-insoluble drug in this case occupies a much larger volume than other compounds.

(10) In the hollow elongated body crystalline morphological form, the water-insoluble drug configuring the crystal exists on the surface of the base material of the balloon. An excipient matrix is not formed in the coating layer on the surface of the base material of the balloon having the water-insoluble drug configuring the crystal. Therefore, the water-insoluble drug configuring the crystal does not adhere to the matrix substance. The water-insoluble drug configuring the crystal is not buried in the matrix substance.

(11) In the hollow elongated body crystalline morphological form, the coating layer may contain crystalline particles of the water-insoluble drug which are regularly arranged on the surface of the base material. The coating layer may also contain excipient particles which are irregularly arranged between the crystalline particles and which are formed of the excipient. The molecular weight of the excipient is smaller than the molecular weight of the water-insoluble drug. Therefore, the proportion occupied by the excipient particles per predetermined area of the base material is smaller than the proportion occupied by the crystalline particles, and the excipient particles do not form a matrix. Here, the crystalline particles of the water-insoluble drug may be one of the above-described elongated bodies. The excipient particles are much smaller than the crystalline particles of the water-insoluble drug and are dispersed between the crystalline particles of the water-insoluble drug. Accordingly, in some cases, the excipient particles cannot be observed using an SEM image or a laser microscope image.

The crystalline layer of the morphological form of the hollow elongated body has low toxicity and an improved stenosis inhibitory effect when the drug is delivered into the body after the surface of the base material of the medical device is coated with the drug as the coating layer. The reason is as follows. The inventor considers that these are affected by solubility and tissue retention after the drug having a particular crystalline morphological form is transferred to the tissue. The water-insoluble drug containing the hollow elongated crystalline form is satisfactorily permeable to the tissue and is satisfactorily soluble since one unit of the crystal becomes small when the drug is transferred to the tissue. Accordingly, the water-insoluble drug can restrain the stenosis by effectively acting on the stenosis. It is additionally conceivable that the drug becomes less toxic since the drug is less likely to remain in the tissue as a large lump.

The layer containing the hollow elongated body crystalline morphological form is the plurality of substantially uniform elongated bodies having the long axis. This layer has the morphological forms which are regularly and substantially uniformly aligned on the surface of the base material. Therefore, the size of the crystal (length in the direction of the longitudinal axis) when transferred to the tissue is as small as approximately 10 µm. The drug can thus uniformly act on the lesion area, thereby improving the tissue permeability. Since the dimension of the crystal to be transferred is small, an excessive amount of the drug does not remain in a target lesion for an excessive amount of time. Accordingly, it is conceivable that an improved stenosis inhibitory effect can be achieved without developing toxicity.

The discharge direction of the dispensing tube 134 (i.e., the discharge direction of the coating solution from the dispensing tube 134) is the direction opposite to the rotation direction of the balloon 30. As a principle in which the water-insoluble drug of the coating layer 32 is formed in the morphological form (including the hollow elongated body crystalline morphological form), it is conceivable that the coating solution discharged from the discharge end 136 onto the balloon 30 may be stimulated by the rotated dispensing tube 134. Then, when a portion (portion of the continuous length in the extending direction of the dispensing tube 134) of the side surface on the end portion side of the dispensing tube 134 is brought into contact with the outer surface of the balloon 30, the coating solution is discharged from the discharge end 136 onto the balloon 30. The dispensing tube 134 and the balloon 30 can thus be brought into proper contact with one another so that the crystal of the water-insoluble drug has the morphological form containing the plurality of elongated bodies each possessing an independent long (longitudinal) axis.

In the region where the balloon 30 is rotated upward in the vertical direction, the coating solution is discharged from the discharge end 136 to the balloon 30. The discharge direction of the dispensing tube 134 (which is likely to discharge the coating solution) can thus be easily set to the direction opposite to the rotation direction of the balloon 30 by causing the dispensing tube to extend downward in the vertical direction.

If the material of the dispensing tube 134 (which comes into contact with the balloon 30) is a polyolefin (polyolefin without containing fluorine) such as polyethylene and polypropylene, organic solvent resistance is lower compared to a dispensing tube 134 made of fluorine resin such as PTFE. The affinity to the organic solvent is high, however, and the contact angle decreases. Accordingly, the coating solution is less likely to be repelled by the characteristics of the material in the discharge end 136 or in the portion in contact with the balloon 30. Therefore, the outer surface of the balloon 30 is less likely to be unevenly coated with the coating solution (in other words, the outer surface of the balloon 30 is thus more likely to be evenly coated with the coating solution). Thus, it is possible to very accurately adjust the uniformity of the coating layer 32. That is, a material whose organic solvent resistance is not higher than the fluororesin resin is specifically used for the dispensing tube 134. The outer surface of the balloon 30 can thus be less likely to be unevenly coated with the coating solution (in other words, even coating is more likely). When the material of the dispensing tube 134 is polyolefin such as polyethylene and polypropylene, at least one of the moving speed of the dispensing tube 134, the discharge speed of the coating solution, and the rotation speed of the balloon 30 is adjusted. In this manner, a configuration can be adopted in which the outer surface of the balloon 30 is unevenly coated with the coating solution. Therefore, the dispensing tube 134 is formed of polyolefin such as polyethylene and polypropylene. In this manner, it is possible to optionally control a degree of uniformity of the coating layer 32.

If the material of the dispensing tube 134 is fluororesin such as PTFE, ETFE, PFA, and FEP, the affinity to the organic solvent is low and the contact angle increases. Accordingly, the coating solution is strongly repelled by the characteristics of the material in the discharge end 136 or in the portion in contact with the balloon 30, which may cause the outer surface of the balloon 30 to be unevenly (non-uniformly) coated with the coating solution. When there is a lot of uneven coating of the coating solution, the amount of the drug in each actually applied location can be increased while the total amount of the drug contained in the coating layer 32 formed in the balloon 30 is equalized (i.e., the same). Therefore, the drug can effectively act on the living body without increasing the burden on the living body. When the uneven coating is regularly and non-uniformly performed, it is preferable that the uneven coating shows a striped pattern (helical filament) in which the linearly applied portions are aligned along the axial direction X of the balloon 30. In the uneven coating, the coating solution is applied while the balloon 30 is rotated with respect to the dispensing tube 134. The coating layer 32 can thus be easily formed while the uneven coating is formed in the stripe pattern. The uneven coating is not limited to the striped pattern. For example, the uneven coating may be in a state where an extremely variable phase is formed.

Both the dispensing tube 134 formed of polyolefin and the other dispensing tube 134 formed of fluorine resin may be used to apply the coating layer 32. The uniformity of the coating layer 32 can thus be controlled by utilizing the above-described different characteristics. When both the dispensing tubes 134 having different characteristics are used (for example, when the balloons 30 of the plurality of balloon catheters 10 are sequentially coated), it is possible to perform control to change the dispensing tube 134 in accordance with the balloon 30. Alternatively, the dispensing tube 134 can be changed depending on the portion of one balloon 30 (i.e., the dispensing tube 134 can be changed for different portions of a single balloon 30).

The drug in coating the outer surface of the balloon 30 can have a different morphological form, such as the crystalline form, the amorphous form, and a mixed form of crystalline and amorphous form. Even when the drug has the crystalline form, there exist various morphological forms having different crystalline structures. Furthermore, crystalline and amorphous materials may be regularly arranged in the coating layer 32 or may be irregularly arranged.

The dispensing tube 134 is gradually moved in the axial direction X while the balloon 30 is rotated. In this manner, the coating layer 32 is gradually formed on the outer surface of the balloon 30 in the axial direction X. After the coating layer 32 is formed in the entire range for coating the balloon 30, the rotary drive unit 110, the pulling unit 150, the linear movement unit 140, and the application unit 130 are stopped.

The balloon catheter 10 is then detached from the balloon coating device 100, and the coating of the outer surface of the balloon 30 is completed.

As described above, one embodiment of the disclosed balloon coating method for forming the coating layer 32 (containing the water-insoluble drug) on the outer surface of the balloon 30 of the balloon catheter 10 has a step of fitting the drive shaft 111 (for rotating the balloon catheter 10) to the opening portion of the three-way stopcock 170 (interlocking member) to be attached to the proximal portion of the hub 40 of the balloon catheter 10 to fix the drive shaft 111 by using the frictional force. The balloon coating method also includes rotating the drive shaft 111 to rotate the balloon 30 around the axis X of the balloon 30 while applying the coating solution containing the drug to the outer surface of the balloon 30. In the balloon coating method configured as described above, the drive shaft 111 is fitted and fixed to the opening portion to be formed in the three-way stopcock 170. Accordingly, the hub 40 is rotated around the central axis of the drive shaft 111, and the balloon 30 can be rotated while the balloon 30 is not shaken if possible (i.e., the balloon 30 can be rotated as smoothly/stably as possible). Therefore, the position of the outer surface of the balloon 30 is less likely to vary (change or deviate) during the rotation. This helps enable a proper quantity of coating solution to be applied to the outer surface of the balloon 30. By having the position of the outer surface of the balloon 30 being less likely to vary during the rotation, it also becomes easier to set a desired value for a contact force of the dispensing tube 134 which is kept in contact with the balloon 30. It thus can be possible to properly set the morphological form of the drug used in coating the balloon 30. The interlocking member is not limited to the three-way stopcock 170, and may be, for example, a dedicated member.

The frictional force between the drive shaft 111 and the three-way stopcock 170 allows the drive shaft 111 to interlock with the three-way stopcock 170 (interlocking member). Accordingly, a predetermined pulling force is applied thereto so that the three-way stopcock 170 is detached from the drive shaft 111. Accordingly, the three-way stopcock 170 can be detached from the drive shaft 111 before being damaged due to an excessive force applied to the balloon 30. Therefore, it is possible to restrain the balloon 30 from being damaged.

The coating solution containing the drug is applied to the outer surface of the balloon 30 while the pulling force is applied to the balloon 30 in the axial direction X of the balloon 30. In this manner, the curvature of the balloon 30 is corrected by the pulling force, so that the rotation force transmitted from the stably rotatable hub 40 is transmitted to the balloon 30. The position of the outer surface of the balloon 30 is thus less likely to vary during the rotation. Accordingly, it is possible to apply a proper quantity of coating solution to the outer surface of the balloon 30, and it becomes easier to set a desired value for the contact force of the dispensing tube 134 which is kept in contact with the balloon 30. Therefore, it is possible to more properly set the morphological form of the drug used in coating the outer surface of the balloon 30.

The drive shaft 111 having the male-luer taper 116 formed in a shape corresponding to the female-luer taper 171 formed in the opening portion of the three-way stopcock 170 (interlocking member) is fitted and fixed to the female-luer taper 171 in the balloon coating method described above. In this manner, the three-way stopcock 170 can be very accurately and easily aligned with the drive shaft 111, thereby allowing the balloon to be stably rotated. The position of the outer surface of the balloon 30 is thus much less likely to vary during the rotation. The male-luer taper 116 of the drive shaft 111 may conform to a standard(s) as described above. Accordingly, various balloon catheters 10 which employ the female-luer taper 171 conforming to the standard(s) can be rotated using the drive shaft 111.

The interlocking member is the three-way stopcock 170. Accordingly, if a lid of the three-way stopcock 170 is switched (opened), the drive shaft 111 can interlock with the hub 40 via the three-way stopcock 170 while the fluid can be injected into or discharged from the balloon 30 via the three-way stopcock 170.

Furthermore, the balloon coating method for forming the coating layer 32 (containing the water-insoluble drug) on the outer surface of the balloon 30 of the balloon catheter 10 described above includes a step of inserting the core 207 into the guide wire lumen 91 penetrating the balloon 30 and causing the distal portion of the core 207 to protrude distally beyond the distal opening portion 93 of the guide wire lumen 91. The balloon coating method also includes disposing the proximal portion of the core 207 proximal to the region (the tubular portion 31 and the tapered portion 33 on both sides)

where the balloon 30 is inflated. The balloon coating method involves pinching and fixing the distal side portion (i.e., distal to the region where the balloon 30 of the balloon catheter 10 is inflated) of the balloon catheter 10, together with the core 207, and a step of moving the dispensing tube 134 relatively to the balloon 30 in the axial direction X of the balloon 30 while rotating the balloon 30 around the axis X of the balloon 30, so as to apply the coating solution from the dispensing tube 134 to the outer surface of the balloon 30. The distal portion of the core 207 is protrudes distal to the distal opening portion 93 of the guide wire lumen 91, and the distal side portion (i.e., distal to the region where the balloon 30 of the balloon catheter 10 is inflated) of the balloon catheter 10 is pinched and fixed together with the core 207. Accordingly, the balloon catheter 10 is restrained (i.e., by the core 207 in the interior of the balloon catheter 10) from being deformed due to collapse when being pinched. The proximal portion of the core 207 is located proximal to the region where the balloon 30 is inflated. Accordingly, the shape of the balloon 30 is effectively corrected by the core 207. It is thus possible to restrain the deformation and damage of the balloon catheter 10, and the position of the outer surface of the balloon 30 is less likely to vary during the rotation, thereby enabling a proper quantity of coating solution to be applied to the outer surface of the balloon 30. This configuration also makes it easier to set a desired value for the dispensing tube 134 contact force applied to the balloon 30, and it is possible to properly set the morphological form of the drug used in coating the balloon 30.

According to the above-described balloon coating method, the balloon catheter 10 is a rapid exchange type. The proximal portion of the core 207 is not caused to protrude from the proximal opening portion 92 of the guide wire lumen 91. The balloon catheter 10 is fixed while the proximal portion of the core 207 is disposed distal to the proximal opening portion 92. In this manner, the core 207 does not interfere with surrounding members when the balloon catheter 10 is rotated. Accordingly, the position of the outer surface of the balloon 30 is less likely to vary during the rotation. Therefore, it is possible to apply a more proper quantity of coating solution to the outer surface of the balloon 30, and it becomes easier to set a desired value for the contact force applied by the dispensing tube 134 to the outer surface of the balloon 30. It is thus possible to more properly set the morphological form of the drug used in coating the balloon 30.

The position of the proximal portion of the core 207 coincides with the proximal end of the balloon 30, or the proximal portion of the core 207 is located proximal to the balloon 30, but does not protrude from the proximal opening portion 92. The core 207 is disposed at a position where the balloon 30 is disposed while the core 207 is prevented from interfering with surrounding members of the core 207 during the rotation. Accordingly, the rotation of the balloon 30 can be stabilized. It is also possible to apply a more proper quantity of coating solution to the outer surface of the balloon 30, and it becomes easier to set a desired value for the contact force of the dispensing tube 134 which is kept in contact with the balloon 30. Therefore, it is possible to more properly set the morphological form of the drug used in coating the balloon 30.

The distance separating (between) the proximal portion of the core 207 and the proximal opening portion 92 is within 50 mm. The core 207 thus does not protrude from the proximal opening portion 92. While the core 207 is prevented from interfering with surrounding members of the core 207 during the rotation, the core 207 is disposed in the widest range of the guide wire lumen 91. Accordingly, the rotation of the balloon 30 can be stabilized. It is thus possible to apply a more proper quantity of coating solution to the outer surface of the balloon 30, and it becomes easier to set a desired value for the contact force of the dispensing tube 134 which is kept in contact with the balloon 30. Therefore, it is possible to more properly set the morphological form of the drug used in coating the balloon 30.

The value obtained by subtracting the outer diameter of the core 207 from the inner diameter of the guide wire lumen 91 exceeds 0 mm, and is 0.5 mm or smaller. In this manner, the core 207 is not larger than the inner diameter of the guide wire lumen 91. Accordingly, it is possible to effectively restrain the damage caused by the core 207 of the inner tube 90 where the guide wire lumen 91 is formed. Furthermore, the core 207 is not significantly smaller than the inner diameter of the guide wire lumen 91, so that it is possible to effectively restrain the deformation of the inner tube 90 when the inner tube 90 is pinched.

The balloon coating method for forming the coating layer 32 containing the water-insoluble drug on the outer surface of the balloon 30 of the balloon catheter 10 has a step of causing at least the two pinching portions 193 (having a groove-like curved surface extending along the axis X of the inner tube 90) to pinch and fix the inner tube 90 penetrating the inside of the balloon 30 of the balloon catheter 10 and the distal joint portion 34 (joint portion) of the balloon 30. The balloon coating method also includes moving the dispensing tube 134 (i.e., the tube for supplying the coating solution containing the drug) relative to the balloon 30 in the axial direction X of the balloon 30 while rotating the balloon 30 (around the axis of the balloon 30), so as to apply the coating solution to the outer surface of the balloon 30. The distal joint portion 34 joining the inner tube 90 and the balloon 30 is pinched and fixed by the pinching portions 193 having the groove-like curved surface. Accordingly, the inner tube 90 or the portion for inflating the balloon 30 is not damaged and the inner tube 90 and the inflatable portion of the balloon 30 can be restrained from being biased (i.e., deviated or displaced). Therefore, the position of the outer surface of the balloon 30 is less likely to vary during the rotation. A proper quantity of coating solution can thus be applied to the outer surface of the balloon 30, it becomes easier to set a desired value for a contact force of the dispensing tube 134 (which is kept in contact with the balloon 30), and it is possible to properly set the morphological form of the drug used in coating the balloon 30.

The balloon 30 is rotated while the balloon 30 is pulled in the axial direction X of the balloon 30 by the pinching portions 193 and while the coating solution containing the drug is applied to the outer surface of the balloon 30. In this manner, the curvature of the balloon 30 is corrected by the pulling force, and the position of the outer surface of the balloon 30 is less likely to vary during the rotation. Therefore, a proper quantity of coating solution can be applied to the outer surface of the balloon 30. In addition, it becomes easier to set a desired value for the contact force of the dispensing tube 134 which is kept in contact with the balloon 30, and it is possible to more properly set the morphological form of the drug used in coating the balloon 30. The gripping force generated by the pinching portions 193 is strengthened in order to apply the pulling force, but the pinching portions 193 have groove-like curved surfaces to grip the distal joint portion 34. Accordingly, damage to the inner tube 90 or the balloon 30 can be restrained.

At least two pinching portions 193 are disposed in the collect chuck 191. The distal joint portion 34 can thus be easily and reliably fixed by the collect chuck 191, and the pulling force can be effectively applied to the balloon 30.

The balloon coating method described above includes applying the rotation force at the same rotational speed to both the proximal side and the distal side of the region (the tubular portion 31 and the tapered portion 33 on both sides) where the balloon 30 of the balloon catheter 10 is inflated and moving the dispensing tube 134 (for supplying the coating solution containing the drug) relative to the balloon 30 in the axial direction X of the balloon 30 while rotating the balloon 30 around the axis X of the balloon 30, so as to apply the coating solution to the outer surface of the balloon 30. The rotation force is applied at the same rotational speed to both the proximal side and the distal side further from the region where the balloon 30 of the balloon catheter 10 is inflated, so that the balloon 30 is less likely to be twisted or biased. The position of the outer surface of the balloon 30 is relatively less likely to vary during the rotation, thereby enabling a proper quantity of coating solution to be applied to the outer surface of the balloon 30. It also accordingly becomes easier to set a desired value for a contact force of the dispensing tube 134 which is kept in contact with the balloon 30, and it is possible to properly set the morphological form of the drug used in coating the balloon 30.

The balloon 30 is rotated while the balloon 30 is pulled in the axial direction X of the balloon 30, thereby applying the coating solution to the outer surface of the balloon 30. In this manner, possible deformation of the balloon catheter 10 is corrected by the pulling force. Accordingly, it is possible to easily apply the rotation force to the balloon catheter 10 from both the proximal portion and the distal portion of the balloon catheter 10.

The distal joint portion 34 of the inner tube 90 (i.e., the tube that penetrates the inside of the balloon 30) and the balloon 30 is pinched and pulled by a pulling force in the axial direction X of the balloon 30. The distal joint portion 34 is thicker than the surrounding portions of the balloon catheter 10, and the outer peripheral surface of the distal joint portion 34 is configured to include the flexible material of the balloon 30. Accordingly, the rotation force can be effectively applied to the balloon catheter 10 via the distal joint portion 34 which is (relatively) easily pinched and through which the rotation force is (relatively) easily applied.

The end portion side where the opening portion for discharging the coating solution is formed in the flexible dispensing tube 134 is brought into contact with the outer surface of the balloon 30 so as to face in the direction opposite to the rotation direction of the balloon 30 while the balloon 30 is rotated around the axis X of the balloon 30. In this state, the coating solution is discharged from the opening portion while the dispensing tube 134 is moved relative to the balloon 30 in the axial direction of the balloon 30, thereby applying the coating solution to the outer surface of the balloon 30. When the dispensing tube 134 (which faces in the direction opposite to the rotation direction of the balloon 30) comes into contact with the outer surface of the balloon 30, the frictional force increases, thereby causing a condition that the balloon 30 is likely to be twisted or biased. However, the rotation force is applied at the same rotational speed to both the proximal portion and the distal portion of the balloon catheter 10. Accordingly, it is possible to adopt a configuration in which the balloon 30 is less likely to be twisted or biased. Therefore, the rotation of the balloon 30 is stabilized while the dispensing tube 134 facing in the direction opposite to the rotation direction of the balloon 30 expedites the crystallization of the water-insoluble drug. It thus becomes easier to set a desired value for the contact force of the dispensing tube 134 which is kept in contact with the balloon 30, and it is possible to properly set the morphological form of the drug used in coating the balloon 30.

The balloon coating method for forming the coating layer 32 containing the water-insoluble drug on the outer surface of the balloon 30 of the balloon catheter 10 having the inflatable balloon 30 in the distal portion of the elongated catheter shaft 20 (shaft) described above includes a step of accommodating the catheter shaft 20 in the groove portion 182 of the support table 181 having the linearly extending groove portion 182, causing the lid portion 183 to close the groove portion 182, and rotatably supporting the catheter shaft 20 inside the groove portion 182. The balloon coating method further includes moving the dispensing tube 134 for supplying the coating solution containing the drug relatively to the balloon 30 in the axial direction of the balloon 30 while rotating the balloon 30 around the axis of the balloon 30, so as to apply the coating solution to the outer surface of the balloon 30. The catheter shaft 20 (shaft) of the balloon catheter 10 is thus rotated inside the groove portion 182 (i.e., while positioned in the groove portion 182). Accordingly, the curvature of the catheter shaft 20 is corrected and accurate rotational movement is achieved. Therefore, the balloon 30 is less likely to be twisted or biased. The position of the outer surface of the balloon 30 is less likely to vary during the rotation, thereby enabling a proper quantity of coating solution to be applied to the outer surface of the balloon 30. It also becomes easier to set a desired value for a contact force of the dispensing tube 134 which is kept in contact with the balloon 30, and it is possible to properly set the morphological form of the drug used in coating the balloon 30. The catheter shaft 20 is accommodated in the groove portion 182, and the groove portion 182 is closed by the lid portion 132. In this simple method, the catheter shaft 20 can be rotated while the curvature of the catheter shaft 20 is corrected, thereby facilitating the coating operation.

The groove portion 182 is located on the extension line of the drive shaft 111 (which applies the rotation force to the hub 40 of the balloon catheter 10). The axis of the drive shaft 111 and the axis of the catheter shaft 20 inside the groove portion 182 coincide with each other in this manner (i.e., the drive shaft 111 and the catheter shaft 20 are coaxial). Accordingly, the rotation of the balloon catheter 10 is stabilized, and the balloon 30 is less likely to be twisted or biased.

At least one of the width and the depth of the groove portion 182 varies depending on the portion of the groove portion 182 (i.e., the width and depth of the groove portion 182 may vary at different segments of the groove portion 182). In this manner, the portion having a different shape and outer diameter of the catheter shaft 20 can be disposed in the groove portions 182 having a different width (e.g., a portion of the catheter shaft 20 that possesses a larger outer diameter can be appropriately positioned in a portion of the groove portion 182 that has a larger width). The rotation of the can be stabilized while wear and damage of the catheter shaft 20 are restrained.

The balloon 30 is rotated by applying the rotation force at the same rotation speed to both the proximal side and the distal side of the balloon catheter 10 while the coating solution is applied. In this manner, even in a condition that the rotation is likely to be unstable due to a frictional force generated by the rotation of the balloon catheter shaft 20 in the groove portion 182, it is possible to apply the rotation force at the same rotation speed to both the proximal side and the distal side of the balloon catheter 10. Accordingly, the balloon 30 is less likely to be twisted or biased. Therefore, the position of the outer surface of the balloon 30 is less likely to vary during the rotation, thereby enabling a proper quantity of coating solution to be applied to the outer surface of the balloon 30. It also becomes easier to set a desired value for the contact force of the dispensing tube 134 which is kept in contact with the balloon 30, and it is possible to properly set the morphological form of the drug used in coating the balloon 30.

The dispensing tube 134 then discharges the coating solution by being brought into contact with the outer surface of the balloon 30 so that the discharge end 136 faces in the direction opposite to the rotation direction of the balloon 30. Accordingly, the water-insoluble drug of the coating layer 32 formed on the outer surface of the balloon 30 can be formed in the morphological form containing the plurality of elongated bodies in which the crystal has each independent long axis. In addition, the dispensing tube 134 discharges the coating solution by being brought into contact with the outer surface of the balloon 30 so that the discharge end 136 faces in the direction opposite to the rotation direction of the balloon 30. Accordingly, the dispensing tube 134 and the balloon 30 are brought into proper contact with each other. Therefore, it is possible to more freely set the morphological form or the size of the drug contained in the coating layer 32.

<Second Embodiment>

Figure 11:
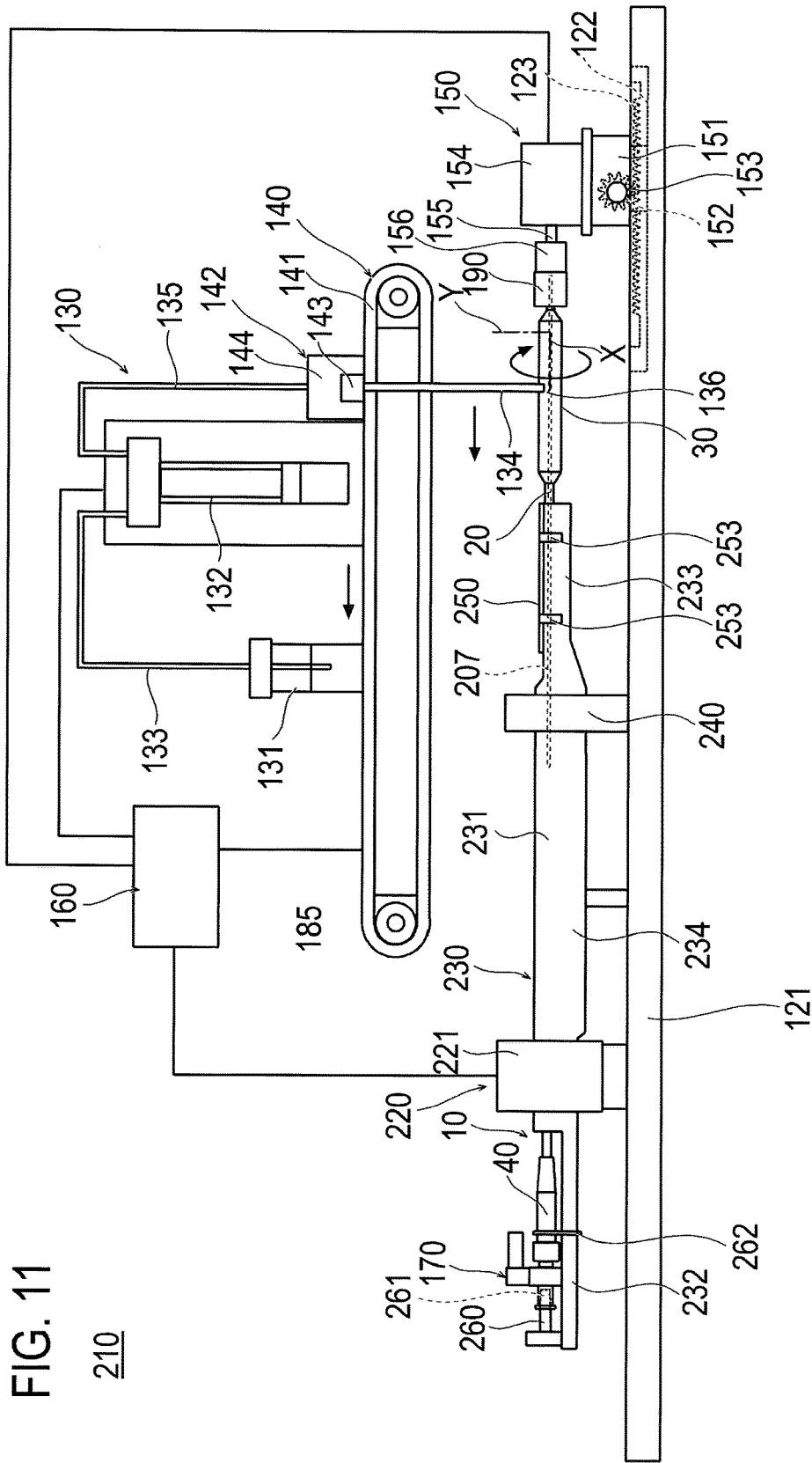
FIG. 11 is a schematic view illustrating a device for carrying out a balloon coating method according to a second embodiment.
Figure 12:
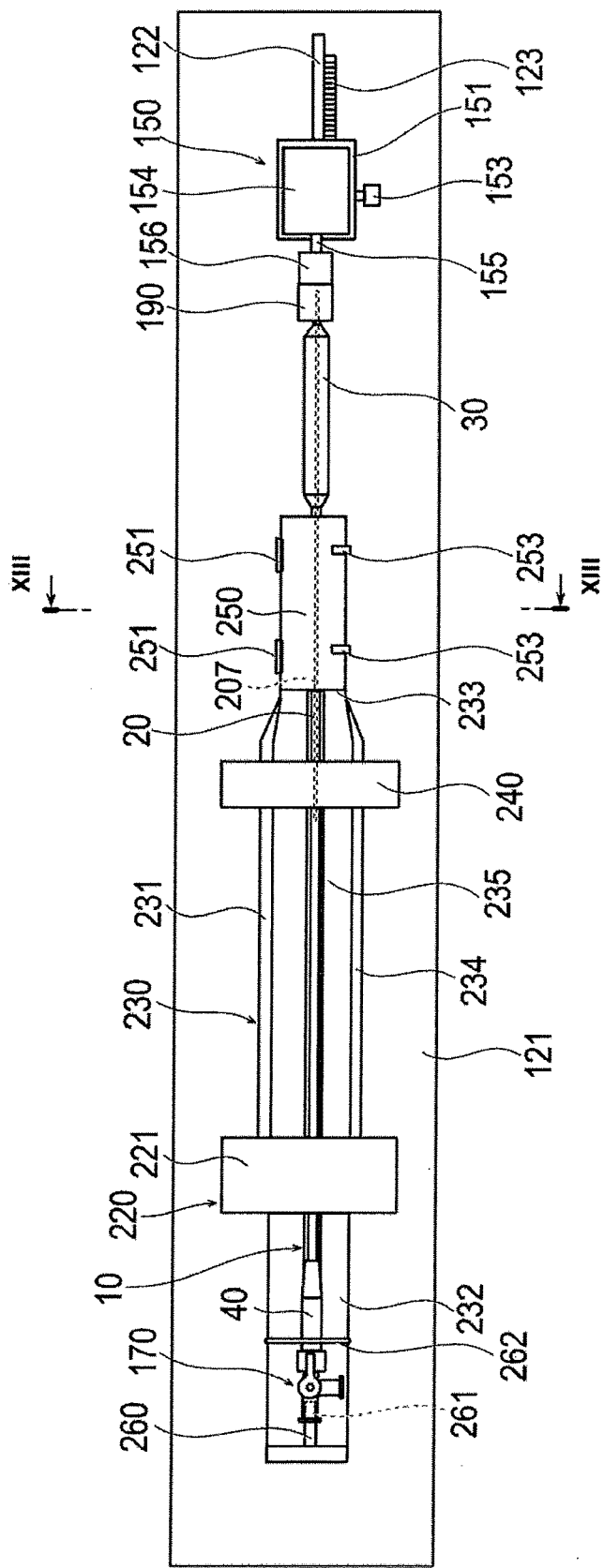
FIG. 12 is a plan view when the device for carrying out the balloon coating method illustrated in FIG. 11 is viewed from above.
Figure 13:
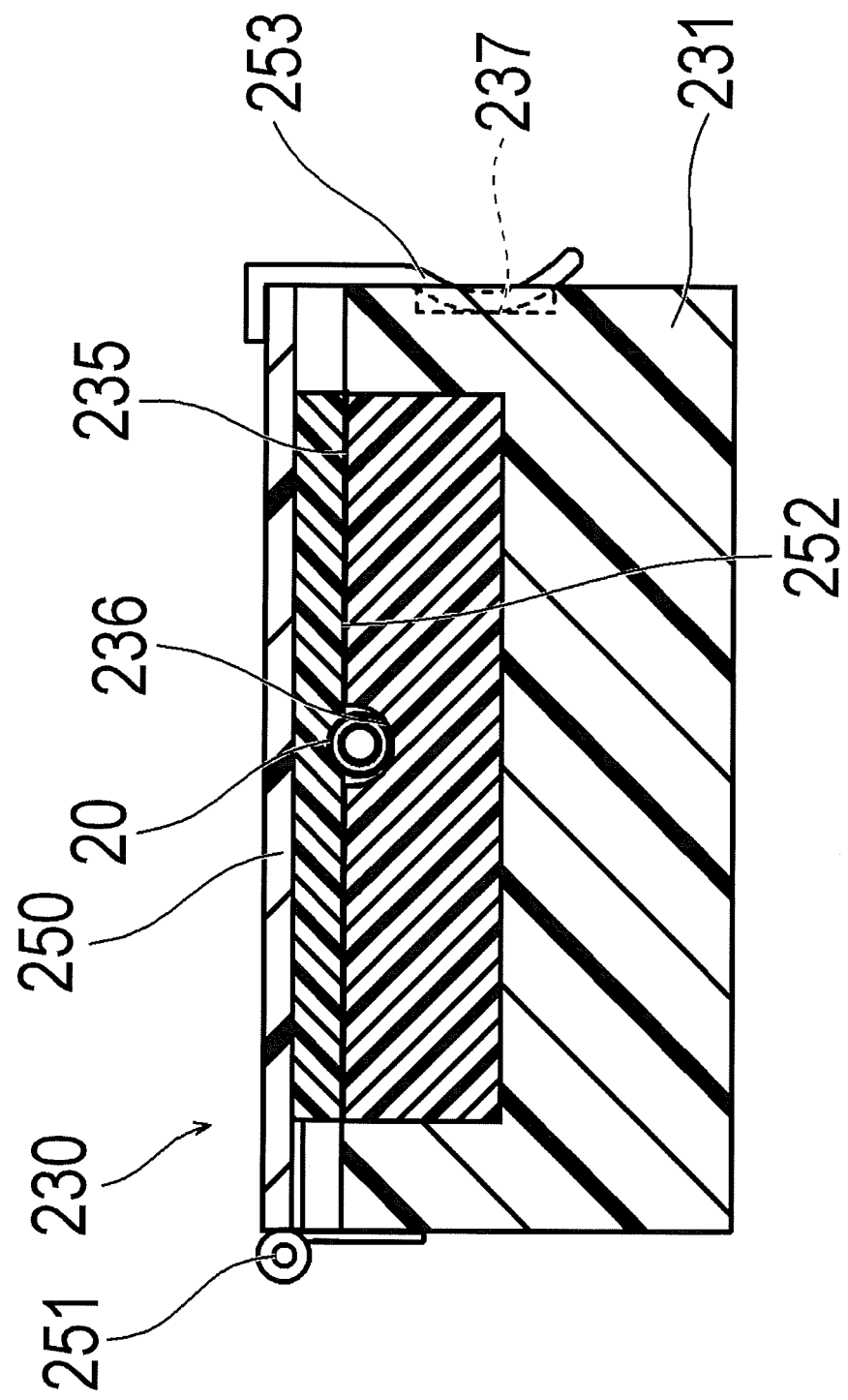
FIG. 13 is a sectional view taken along line XIII-XIII in FIG. 12.
Figure 14:
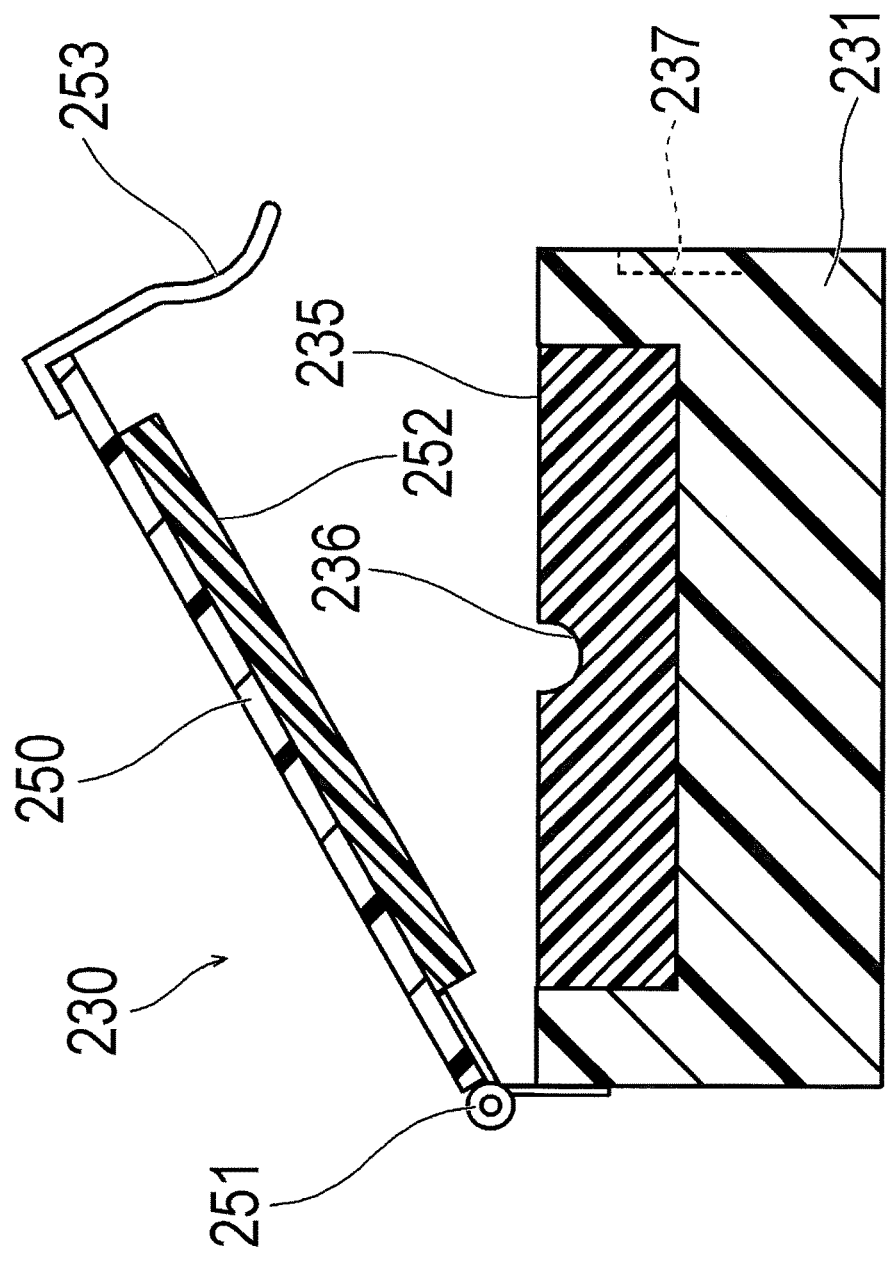
FIG. 14 is a sectional view illustrating a state where a lid portion is open.

In a balloon coating method according to a second embodiment, the balloon catheter 10 is held in a rotatable support unit and the balloon catheter 10 is rotated together with the rotatable support unit, thereby forming the coating layer 32 containing the water-insoluble drug on the outer surface of the balloon 30. The balloon coating method according to the second embodiment is carried out by a balloon coating device 210 illustrated in FIGS. 11 and 12. The same reference numerals will be given to elements having the same functions as those according to the first embodiment, and repeated description of the same elements will be omitted.

The balloon coating device 210 includes a rotary drive unit 220 (first rotary drive unit) that applies the rotation force to the balloon catheter 10, a support unit 230 that supports the balloon catheter 10, and a bearing portion 240 that rotatably supports the support unit 230. The balloon coating device 210 includes a foundation table 121, an application unit 130 having the dispensing tube 134, a linear movement unit 140 that moves the dispensing tube 134, a pulling unit 150 (secondary rotary drive unit), and a control unit 160 that controls the balloon coating device 210.

The rotary drive unit 220 includes a first motor 221. The first motor 221 is fixed to the foundation table 121 to rotatably hold the support unit 230.

The support unit 230 penetrates the first motor 221 (i.e., extends into the first motor 221) and is rotatably held by the first motor 221. The support unit 230 includes a support table 231 which holds the balloon catheter 10, and a lid portion 250 which pinches the balloon catheter 10 together with the support table 231. Furthermore, the support unit 230 includes a hinge portion 251 which interlocks the lid portion 250 with the foundation table 121 in an openable and closable manner. The support unit 230 also includes a support shaft 260 inserted into the three-way stopcock 170 attached to the balloon catheter 10.

The support table 231 includes a support table proximal portion 232 which penetrates the first motor 221, a support table distal portion 233 that interlocks with the lid portion 250, and a support table central portion 234 formed between the support table proximal portion 232 and the support table distal portion 233.

The support table proximal portion 232 supports the proximal portion of the balloon catheter 10 and penetrates the first motor 221. The support table proximal portion 232 is fixed to the support shaft 260 proximal to the first motor 221. The support shaft 260 is inserted into the three-way stopcock 170 attached to the balloon catheter 10, thereby fixing the proximal portion of the balloon catheter 10. The three-way stopcock 170 is attached to the hub 40. The three-way stopcock 170 is openable to allow the inflating fluid to be introduced to flow into the balloon 30, thereby inflating the balloon 30. The three-way stopcock 170 can then be closed to maintain the balloon 30 in an inflated state.

The support table distal portion 233 supports the distal portion of the catheter shaft 20 and is located distal to the bearing portion 240. The lid portion 250 interlocks with the support table distal portion 233 so as to be pivotable (rotatable) about the hinge portion 251. The support table distal portion 233 has a support surface 235 formed of a flexible material so that the catheter shaft 20 can be pinched between the lid portion 250 and the support surface 235. The support surface 235 has a groove portion 236 for partially accommodating a portion of the catheter shaft 20 so that the catheter shaft 20 can be pinched (held) at a proper position. The lid portion 250 has a pressing surface 252 formed of a flexible material to pinch the catheter shaft 20 between the support surface 235 and the pressing surface 252. The support surface 235 and the pressing surface 252 are elastically deformed when pinching the catheter shaft 20 therebetween (i.e., between the support surface 235 and the pressing surface 252), thereby holding the catheter shaft 20 by using an elastic force. The support surface 235 and the pressing surface 252 material(s) is, for example, foamed polyurethane or foamed polyethylene. A side surface of the support table distal portion 233 has a concave portion 237 which can interlock with a lock mechanism 253 disposed in the lid portion 250 in order to fix the lid portion 250 to the support table distal portion 233. For example, the lock mechanism 253 is a snap fit.

The support table central portion 234 has the support surface 235 which supports the catheter shaft 20, penetrates the bearing portion 240, and is rotatably supported by the bearing portion 240.

It is preferable that the width and the depth of the groove portion 236 are approximately 0.5 to 3.5 mm smaller than the outer diameter of the catheter shaft 20 so that the catheter shaft 20 can be pinched between the lid portion 250 and the groove portion 236.

In the present embodiment, the bottom surface of the groove portion 236 has a semicircular shape in a cross section orthogonal to the axial direction X. The groove portion 236 is not limited to having a semicircular shape, however, and the groove portion 236 may have, for example, a V-shape or a rectangular shape. It is preferable that the groove portion 236 has a shape which contacts the outer surface of the catheter shaft 20 so that the catheter shaft 20 is less likely to be damaged. Therefore, it is preferable that the shape of the groove portion 236 does not include a protruding portion so as to have a W-shape (in a cross section orthogonal to the axial direction X). The groove portion 236 also may not be formed in some embodiments.

The lid portion 250 is pivotably held on the support table distal portion 233 by the hinge portion 251. The lid portion 250 can close the groove portion 236 (i.e., close the open top of the groove portion 236) by covering the support surface 235. The lid portion 250 is also operable to expose the groove portion 236 by being separated from the support surface 235 (i.e., rotated open). The lid portion 250 has the pressing surface 252 that pinches the catheter shaft 20 between the pressing surface 252 and the support surface 235.

The core 207 is disposed inside the guide wire lumen 91 of the balloon catheter 10. The distal portion of the core 207 protrudes distally beyond (i.e., distal relative to) the distal opening portion 93 of the guide wire lumen 91. The proximal portion of the core 207 is located proximal to the position pinched by the support surface 235 and the pressing surface 252. The protrusion length of the core 207 beyond the distal opening portion 93 is not particularly limited. In order to restrain the collapse of the balloon catheter 10 when the balloon catheter 10 is pinched by the collect chuck 191, however, it is preferable that the length enables the core 207 to reliably protrude. For example, the core 207 length is 2 to 50 mm.

The distal portion of the core 207 protrudes distally beyond the distal opening portion 93 of the guide wire lumen 91, and the proximal portion of the core 207 is located on the proximal side of the balloon 30. Accordingly, the core 207 exists inside the portion pinched by the pinching portion 193, thereby restraining deformation caused by the collapse of the balloon catheter 10.

The proximal portion of the core 207 is located proximal to the position pinched by the support table 231 having the support surface 235 and the lid portion 250 having the pressing surface 252. Accordingly, the core 207 exists inside the portion pinching by the support surface 235 and the pressing surface 252, thereby restraining deformation caused by the collapse of the balloon catheter 10.

The distal portion of the support shaft 260 has a male-luer taper 261 whose diameter decreases in the distal direction (i.e., the outer diameter of the male-luer taper 261 tapers or gradually decreases in the distal direction). The male-luer taper 261 is inserted into a female-luer taper 171 formed in the three-way stopcock 170, and can be fitted (connected) to the female-luer taper 171 using a frictional force. A taper rate of the male-luer taper 261 and the female-luer taper 171 is stipulated by ISO 594 or JIS (Standardized Commentary Explanation of Medical Equipment), in which the taper rate is stipulated as 6%. A range into which the support shaft 260 is inserted is within a range of the three-way stopcock 170. The support shaft 260 can thus easily be attached to and detached from the three-way stopcock 170, improving convenience.

The male-luer taper 261 of the support shaft 260 may be inserted into and fitted to a female-luer taper 171 formed in the hub proximal opening portion 41 of the hub 40, instead of the female-luer taper 171 being formed in the three-way stopcock 170. The support shaft 260 is not inserted to extend distally beyond the hub 40. In this manner, the support shaft 260 is easily attached to and detached from the hub 40, thereby improving convenience.

The control unit 160 is configured to include, for example, a computer and comprehensively controls the rotary drive unit 220, the linear movement unit 140, the pulling unit 150, and the application unit 130. The control unit 160 can synchronously rotate the first motor 221 of the rotary drive unit 220 and the second motor 154 of the pulling unit 150 at the same rotation speed. The control unit 160 can also comprehensively control the rotation speed of the balloon 30, the initial positioning of the dispensing tube 134 with respect to the balloon 30, the moving speed of the dispensing tube 134 relative to the balloon 30 in the axial direction X, and the drug discharge speed from the dispensing tube 134.

Next, the balloon coating method for forming the coating layer 32 containing the water-insoluble drug on the surface of the balloon 30 by using the above-described balloon coating device 210 will be described.

First, the three-way stopcock 170 interlocks with the hub proximal opening portion 41 of the hub 40 of the balloon catheter 10, and the three-way stopcock 170 is opened. A syringe is used to introduce inflating fluid which flows into the balloon 30. After the balloon 30 is inflated, the three-way stopcock 170 is closed to maintain the balloon 30 in an inflated state. It is also possible to form the coating layer 32 on the surface of the balloon 30 without inflating the balloon 30. In this case, it is not necessary to supply the inflating fluid into the balloon 30.

The lid portion 250 interlocking with the support table 231 is then opened, and the catheter body 20 is accommodated inside (i.e., placed in or positioned in) the groove portion 236. The lid portion 250 is closed, and a closed state is maintained by the lock mechanism 253 (i.e., the lock mechanism 253 locks the lid portion 250 in the closed position). In this manner, the catheter shaft 20 is pinched and fixed between the support surface 235 and the pressing surface 252 while the elastically deformable support surface 235 and pressing surface 252 are flexibly deformed. The core 207 passes through the range pinched between the support surface 235 and the pressing surface 252 of the catheter shaft 20. Accordingly, the catheter shaft 20 can be restrained from being deformed.

Next, the male-luer taper of the support shaft 260 is inserted into the female-luer taper 171 to interlock with the female-luer taper 171 of the three-way stopcock 170. The hub 40 can thus be stably held by the support table 231 during the rotation. In addition, as a supplementary method, the catheter shaft 20 can be fixed to the support table proximal portion 232 by using a wire member 262 such as a rubber band and a wire.

Next, the distal joint portion 34 of the balloon catheter 10 is pinched by the pinching portions 193 of the collect chuck 191. The rotation force of the second motor 154 can thus be applied to the distal portion of the balloon catheter 10.

The order for installing the balloon catheter 10 in the support shaft 260, the collect chuck 191, and the support table 231 is not particularly limited.

If the dial 153 is rotated and the second motor 154 and the collect chuck 191 are moved in the distal direction (i.e., distally in the axial direction), the pulling force is applied to the balloon catheter 10, and the curvature of the balloon 30 is corrected. The catheter shaft 20 is pinched between the support surface 235 and the pressing surface 252 when this pulling force is applied to the balloon catheter 10. Accordingly, the pulling force is not applied to the proximal side further from the pinched portion of the catheter shaft 20.

Next, the drive unit 144 is operated, and the dispensing tube 134 is aligned with the balloon 30. Specifically, the dispensing tube 134 approaches (moves toward) the outer surface of the balloon 30, is pressed against the outer surface of the balloon 30 to contact and deform against the outer surface balloon 30. More specifically, the side surface on the end portion side (dispensing end) of the dispensing tube 134 contacts the outer surface of the balloon 20.

The coating solution is supplied to the dispensing tube 134 while the liquid feeding amount is adjusted by the liquid feeding pump 132, and the balloon catheter 10 is rotated together with the support table 231 by the first motor 221 and the second motor 154. The movable carriage 141 thereafter moves proximally in the axial direction to gradually move the dispensing tube 134 in the proximal direction along the axial direction X. The coating solution discharged from the discharge end 136 of the dispensing tube 134 is thus spirally applied to the outer peripheral surface of the balloon 30 by the dispensing tube 134 moving relative to the balloon 30.

The balloon catheter 10 is pinched between the pressing surface 252 and the support surface 235. Accordingly, the portion on the proximal side further from the pinched position does not affect the rotation of the balloon 30. Therefore, the curvature and eccentricity of the proximal side further from the pinched position between the pressing surface 252 and the support surface 235 of the balloon catheter 10 are not strictly restricted. Relatively stable rotation of the balloon 30 can accordingly be realized. Fluctuations in the thickness of the applied coating solution can be restrained, and the thickness or the morphological form of the coating layer 32 is easily adjusted.

The solvent contained in the coating solution applied to the outer surface of the balloon 30 is then volatilized, and the coating layer 32 containing the water-insoluble drug is formed on the surface of the balloon 30.

The extending direction (discharge direction) of the dispensing tube 134 extending toward the discharge end 136 is the direction opposite to the rotation direction of the balloon 30. Accordingly, the water-insoluble drug of the coating layer 32 formed on the outer surface of the balloon 30 is formed to contain the morphological form containing the plurality of elongated bodies in which the crystal has each independent long axis.

The drug coated on the outer surface of the balloon 30 can be a different morphological form, such as crystalline, amorphous, and a mixed form. Even when the drug has the crystalline form, there exist various morphological forms having different crystalline structures. Crystalline and amorphous materials may be regularly arranged in the coating layer 32, but also may be irregularly arranged.

The dispensing tube 134 is gradually moved proximally in the axial direction X while the balloon 30 is rotated. In this manner, the coating layer 32 is gradually formed on the outer surface of the balloon 30 along the axial direction X. After the coating layer 32 is formed in the entire range for coating the balloon 30, the rotary drive unit 220, the linear movement unit 140, the pulling unit 150, and the application unit 130 are stopped.

Thereafter, the balloon catheter 10 is detached from the balloon coating device 210, and the coating of the balloon 30 is completed.

As described in the second embodiment of the balloon coating method, the balloon coating method (for forming the coating layer 32 containing the water-insoluble drug on the outer surface of the balloon 30 of the balloon catheter 10 having the inflatable balloon 30 in the distal portion of the elongated catheter shaft 20) (shaft) includes holding the catheter shaft 20 in the support unit 230 rotatable around the axis X of the balloon 30 (i.e., holding the catheter shaft 20 within the support unit 230 while the catheter shaft 20 remains rotatable within the support unit 230). The balloon coating method includes moving the dispensing tube 134 (for supplying the coating solution containing the drug) relative to the balloon 30 in the axial direction X of the balloon 30 while rotating the balloon 30 together with the support table 231, so as to apply the coating solution to the outer surface of the balloon 30.

The balloon 30 is rotated in a state where the catheter shaft 20 is held by the rotatable support unit 230. Accordingly, the curvature of the catheter shaft 20 is less likely to affect the rotation of the balloon 30, and the balloon 30 is less likely to be twisted or biased. Therefore, the position of the outer surface of the balloon 30 is less likely to vary during the rotation, thereby enabling a proper quantity of coating solution to be applied to the outer surface of the balloon 30. It also becomes easier to set a desired value for the contact force of the dispensing tube 134 which is kept in contact with the balloon 30, and it is possible to properly set the morphological form of the drug used in coating the balloon 30.

The support unit 230 has the support table 231 having the linear groove portion 236 capable of accommodating at least portion of the catheter shaft 20 (shaft), and the lid portion 250 capable of covering the groove portion 236. In the step of holding the catheter shaft 20, the catheter shaft 20 is accommodated in the groove portion 236, and the lid portion 250 covers the groove portion 236. In this manner, the catheter shaft 20 is held by the support unit 230. The catheter shaft 20 can thus be held easily and reliably held so as not to fall out from (i.e., unintentionally be displaced from) the groove portion 236.

The catheter shaft 20 is pinched by the support table 231 and the lid portion 250. In this manner, the catheter shaft 20 can be firmly held by the support unit 230. Accordingly, the rotation of the balloon 30 is stabilized, and the balloon 30 is less likely to be twisted or biased.

The catheter shaft 20 is held by the support unit 230 in a state where the core 207 inserted into the catheter shaft 20. In this manner, even if the catheter shaft 20 is held by the support unit 230, the catheter shaft 20 can be restrained from being deformed.

The balloon catheter 10 is rotatably supported by the bearing portion 240 disposed distal to the rotary drive unit 220 while the balloon catheter 10 is rotated by the rotary drive unit 220 which applies the rotation force to the support unit 230. In this manner, the rotation of the support unit 230 extending from the rotary drive unit 220 in the distal direction is stabilized. Accordingly, the rotation of the balloon 30 is stabilized, and the balloon 30 is less likely to be twisted or biased.

The disclosed balloon coating method, balloon rotating method, and balloon coating device are not limited to only the above-described embodiments, and various modifications are possible by those skilled in the art within the technical idea of the present disclosure. For example, in the above-described first and second embodiments, the coating solution is applied from the distal side of the balloon 30 to the proximal side. However, the coating solution may instead be applied from the proximal side to the distal side (i.e., with the dispensing tube 134 beginning at the proximal end and gradually moving toward the distal end of the balloon 30).

In addition, in the above-described embodiments, the dispensing tube 134 extends downward along the vertical direction, and comes into contact with the outer surface of the balloon 30. However, the extending direction of the dispensing tube 134 is not particularly limited. For example, the dispensing tube 134 may be inclined with respect to the vertical direction, or may extend laterally or upward.

The balloon coating method described above involves coating a balloon 30 of the balloon catheter 10 of a rapid exchange type. However, the coating may be performed on the balloon of the balloon catheter of an over-the-wire type in which a guide wire lumen is formed from the hub to the distal portion.

Figure 15:
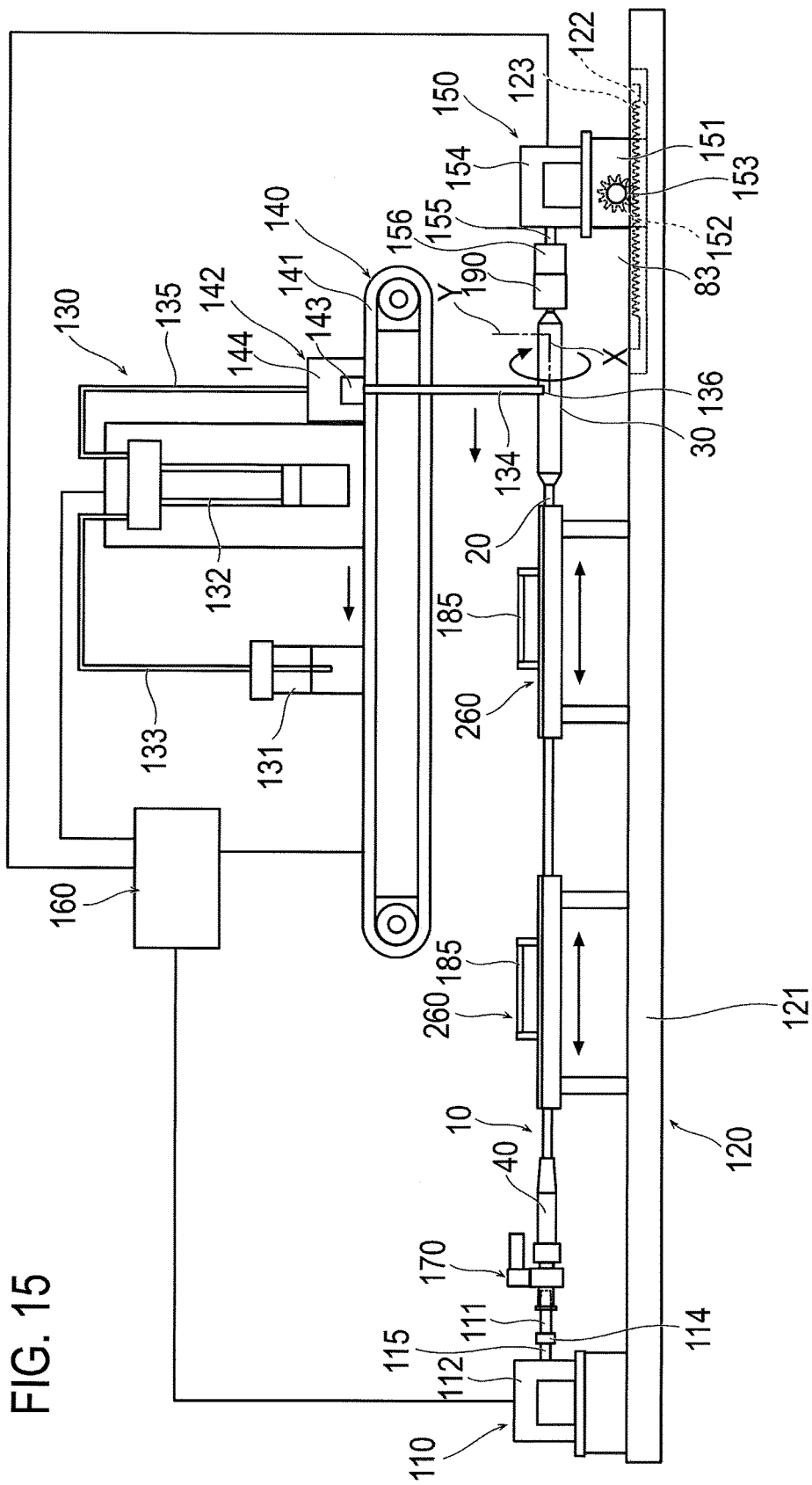
FIG. 15 is a schematic view illustrating a modification example of the balloon coating device illustrated in FIG. 1.

A modification example of the first embodiment is also illustrated in FIG. 15. A plurality of (the two in the example of FIG. 15) the support units 260 which rotatably support the catheter shaft 20 may be provided. Then, the support unit 260 may be optionally movable along the axis X of the balloon 30 (that is, along the extending direction of the groove portion disposed in each of the support units 260). The plurality of the support units 260 are disposed side by side along the extending direction of the groove portion disposed in each of the support units 260.

In this way, the catheter shaft 20 is supported by the plurality of the support units 260. Accordingly, it is possible to reduce the friction between the support unit 260 and the catheter shaft 20. While the wear and damage of the catheter shaft 20 are restrained, the rotation of the catheter shaft 20 can be stabilized.

The support unit 260 is movable. Accordingly, the support unit 260 can be moved before supporting the catheter shaft 20. In this manner, the catheter shaft 20 can be supported at a desired position, and the rotation of the balloon catheter 10 can be stabilized.

In addition, a plurality of the lid portions may be disposed in one support table.

The detailed description above describes a balloon coating method, a balloon rotating method, and a balloon coating device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon coating method for forming a coating layer containing a drug on an outer surface of a balloon of a balloon catheter, the balloon catheter extending in an axial direction and possessing a longitudinal axis, the method comprising:
    applying a first rotation force to the balloon catheter at a first position proximal to the balloon of the balloon catheter, the balloon being a region of the balloon catheter that is inflatable radially outward and deflated radially inward, the first rotation force being applied at a first rotation speed;
    applying a second rotation force to the balloon catheter at a second position distal to the balloon of the balloon catheter, the second rotation force being applied simultaneously while the first rotation force is being applied to the balloon catheter at the first position to rotate the balloon catheter about the longitudinal axis of the balloon catheter, the second rotation force being applied at a second rotation speed;
    the first rotation speed being the same as the second rotation speed; and
    applying a coating solution containing the drug to the outer surface of the balloon from a dispensing tube while gradually moving the dispensing tube in the axial direction and simultaneously applying the first and second rotation forces to rotate the balloon catheter around the longitudinal axis of the balloon catheter,
    wherein the dispensing tube comprises an open end and an outer peripheral surface, the outer peripheral surface at the open end of the dispensing tube contacting the outer surface of the balloon when the coating solution is being applied while the balloon is rotated around the axis of the balloon, the coating solution being applied from the open end in a direction opposite to a rotation direction of the balloon.

2. The balloon coating method according to claim 1, further comprising:
    applying a pulling force to the balloon catheter in the axial direction of the balloon catheter while the coating solution containing the drug is being applied to the outer surface of the balloon.

3. The balloon coating method according to claim 2, wherein
    the balloon possesses an interior and an inner surface,
    the balloon catheter comprises an inner tube penetrating through the interior of the balloon and a joint portion connecting the inner surface of the balloon to an outer surface of the inner tube, and
    the pulling force is applied to the joint portion so that the balloon is pinched and pulled so as to apply the pulling force to the balloon.

4. The balloon coating method according to claim 2, wherein the pulling force pulls the balloon distally in the axial direction.

5. The balloon coating method according to claim 4, wherein the pulling force is 5 N-15 N.

6. The balloon coating method according to claim 5, wherein
    the balloon catheter comprises a hub, and
    the first rotation force is applied by a drive shaft connected to the hub of the balloon catheter via an interlocking member.

7. The balloon coating method according to claim 6, wherein
    the drive shaft comprises an outer surface and the interlocking member comprises an inner surface,
    the drive shaft is fixed to the interlocking member by fitting the outer surface of the drive shaft into the inner surface of the interlocking member to create a frictional force between the outer surface of the drive shaft and the inner surface of the interlocking member, and
    the frictional force created between the outer surface of the drive shaft and the inner surface of the interlocking member is 10 N-50 N.

8. The balloon coating method according to claim 1, wherein the first rotation speed and the second rotation speed is 10 rpm to 300 rpm.

9. The balloon coating method according to claim 1, wherein the drug is water-insoluble.

10. A balloon rotating method for rotating a balloon catheter, comprising:
    applying a first rotation force to the balloon catheter, the balloon catheter comprising an elongated shaft extending in an axial direction, a longitudinal axis, and a balloon connected to the elongated shaft, the balloon being expandable radially outward and deflatable radially inward, the balloon comprising a distal end and a proximal end, the first rotation force being applied proximal to the proximal end of the balloon of the balloon catheter at a first rotation speed;
    applying a second rotation force to the balloon catheter distal to the distal end of the balloon of the balloon catheter, the second rotation force being applied simultaneously while the first rotation force is being applied to the balloon catheter to rotate the balloon about the longitudinal axis of the balloon catheter, the second rotation force being applied at a second rotation speed;
    the first rotation speed being the same as the second rotation speed;

applying a pulling force to the balloon catheter to pull the elongated shaft of the balloon catheter distally in the axial direction of the balloon catheter while the balloon is rotated; and the balloon possessing an interior and an inner surface, the elongated shaft penetrating through the interior of the balloon, the balloon catheter comprising a joint portion connecting the inner surface at the distal end of the balloon to an outer surface of the elongated shaft, and the pulling force being applied to the joint portion so that the balloon is pinched and pulled distally in the axial direction.

11. The balloon rotating method according to claim 10, wherein, before the rotating of the balloon catheter, the balloon rotating method comprises:

positioning at least a portion of the elongated shaft of the balloon catheter in a support table, the support table comprising a groove and a lid, the lid being opened when the elongated shaft is positioned within the groove of the support table, and closing the lid of the support table to rotatably support the elongated shaft of the balloon catheter within the groove such that the elongated shaft stably rotates within the groove when the first and second rotation forces are applied to the balloon catheter to rotate the balloon about the longitudinal axis of the balloon catheter.

12. The balloon rotating method according to claim 10, wherein the first rotation speed and the second rotation speed is 10 rpm to 300 rpm.

13. A balloon coating device for forming a coating layer containing a drug on an outer surface of a balloon of a balloon catheter, the device comprising:

a first rotary drive unit configured to apply a first rotation force to the balloon catheter, the balloon catheter comprising an elongated shaft extending in an axial direction and a balloon connected to the elongated shaft, the balloon being expandable radially outward and deflatable radially inward, the balloon comprising a distal end and a proximal end, the first rotary drive unit applying the first rotation force at a first position proximal to the proximal end of the balloon of the balloon catheter at a first rotation speed;

a second rotary drive unit configured to apply a second rotation force to the balloon catheter at a second position distal to the distal end of balloon, the second rotatory drive unit applying the second rotation force at a second rotation speed, the second rotary drive unit being configured to apply the second rotation force while the first rotatory drive unit applies the first rotation force;

the first rotation speed applied by the first rotary drive unit being equal to the second rotation speed applied by the second rotary drive unit;

a container storing a coating solution containing the drug;

a movable carriage configured to move in the axial direction;

a dispensing tube connected to the container for applying the coating solution containing the drug to the outer surface of the balloon to form the coating layer on the outer surface of the balloon, the dispensing tube being connected to the movable carriage so that movement of the carriage in the axial direction results in movement of the dispensing tube in the axial direction; and a pulling unit that applies a pulling force in the axial direction of the balloon while the first and second rotary drive units rotate the balloon catheter, wherein the balloon possesses an interior and an inner surface, the elongated shaft penetrating through the interior of the balloon, the balloon catheter comprises a joint portion connecting the inner surface at the distal end of the balloon to an outer surface of the elongated shaft, and the pulling unit applies the pulling force at the joint portion so that the balloon is pinched and pulled distally in the axial direction while the first and second rotary drive units rotate the balloon catheter.

14. The balloon coating device according to claim 13, wherein the pulling unit comprises a chuck configured to compress radially inwardly to clamp onto the joint portion and to expand radially outwardly to release the joint portion of the balloon catheter.

15. The balloon coating device according to claim 13, wherein the first rotation speed applied by the first rotary drive unit and the second rotation speed applied by the second rotary drive unit is 10 rpm to 300 rpm.

16. The balloon coating device according to claim 13, wherein the drug is water-insoluble.

* * * * *